(12) United States Patent
Plaitakis

(10) Patent No.: US 8,361,728 B2
(45) Date of Patent: Jan. 29, 2013

(54) METHOD FOR DIAGNOSIS OF GLUTAMATE DEHYDROGENASE DISORDERS

(76) Inventor: Andreas Plaitakis, Crete (GR)

( * ) Notice: Subject to any disclaimer, the term of this patent is extended or adjusted under 35 U.S.C. 154(b) by 587 days.

(21) Appl. No.: 12/459,179

(22) Filed: Jun. 25, 2009

(65) Prior Publication Data

US 2010/0166880 A1 Jul. 1, 2010

Related U.S. Application Data

(60) Provisional application No. 61/133,221, filed on Jun. 26, 2008.

(51) Int. Cl.
*C12Q 1/68* (2006.01)
*G01N 33/68* (2006.01)
(52) U.S. Cl. .................... 435/6.16; 435/6.11; 435/6.12
(58) Field of Classification Search .................. None
See application file for complete search history.

(56) References Cited

U.S. PATENT DOCUMENTS 5,028,622 A 7/1991 Plaitakis
2006/0263453 A1 11/2006 Smith et al.

OTHER PUBLICATIONS

Zaganas, et al., "Substitution of Ser for Arg-443 in the Regulatory Domain of Human Housekeeping (*GLUD*1) Glutamate Dehydrogenase Virtually Abolishes Basal Activity and Markedly Alters the Activiation of the Enzyme by ADP and L-Leucine," *The Journal of Biological Chemistry*, vol. 277, No. 48, pp. 46552-46558, Nov. 29, 2002.
Kanavouras, et al. "Properties and Molecular Evolution of Human *GLUD*2 (Neural and Testicular Tissue-Specific) Glutamate Dehydrogenase," *Journal of Neuroscience Research* 85, pp. 1101-1109, 2007).
Plaitakis, et al. Study of Structure-Function Relationships in Human Glutamate Dehydrogenases Reveals Novel Molecular Mechanisms for the Regulation of the Nerve Tissue-Specific (*GLUD*2) Isoenzyme), *Neurochemistry International*, pp. 401-410, 2003.
Panov, et al., "Rotenone Model of Parkinson Disease," *The Journal of Biological Chemistry*, vol. 280, No. 51, pp. 42026-42035, Dec. 23, 2005.

*Primary Examiner* — Robert C Hayes
(74) *Attorney, Agent, or Firm* — Schafer Smith LLC

(57) ABSTRACT

Methods and compositions for diagnosis and treatment of neurodegenerative disorders are disclosed. The methods and compositions apply the discovery of the correlation between an hGDH2 gene polymorphism and the occurrence of atypical Parkinson's Disease.

7 Claims, 12 Drawing Sheets hGDH2

METHOD FOR DIAGNOSIS OF GLUTAMATE DEHYDROGENASE DISORDERS

RELATED APPLICATION

The present application claims the benefit of the filing date under 35 U.S.C. §119(e) of Provisional U.S. Patent Application Ser. No. 61/133,221, filed Jun. 26, 2008, which is hereby incorporated by reference.

BACKGROUND

Parkinson's disease (PD) affects about 1.8% of people over the age of 65[1]. It is clinically characterized by tremor, rigidity and bradykinesia that often occur along with disturbances of posture and gait. About 80% of PD cases are sporadic with males being more frequently affected than females (ratio=1.5:1). Patients with PD experience a clinical worsening over time.

Current treatments aim mainly at restoring dopaminergic transmission in the basal ganglia. These treatments are capable of alleviating some of the symptoms of the disorder (at least for several years after onset). However, no approach is presently known that can alter the progressive course of the neurodegenerative process and, consequently, the plethora of the clinical deficits associated with this degeneration.

BRIEF SUMMARY

Methods and compositions for diagnosing and treating neurodegenerative disorders are provided. The methods utilize the surprising discovery of a correlation between a glutamate dehydrogenase gene polymorphism and the onset and progression of Parkinson's disease. The methods also utilize the discovery that estrogens show a higher affinity for hGDH2 than for hGDH1.

Other systems, methods, features and advantages of the invention will be, or will become, apparent to one with skill in the art upon examination of the following figures and detailed description. It is intended that all such additional systems, methods, features and advantages be included within this description, be within the scope of the invention, and be protected by the following claims.

DETAILED DESCRIPTION

Figure 1:
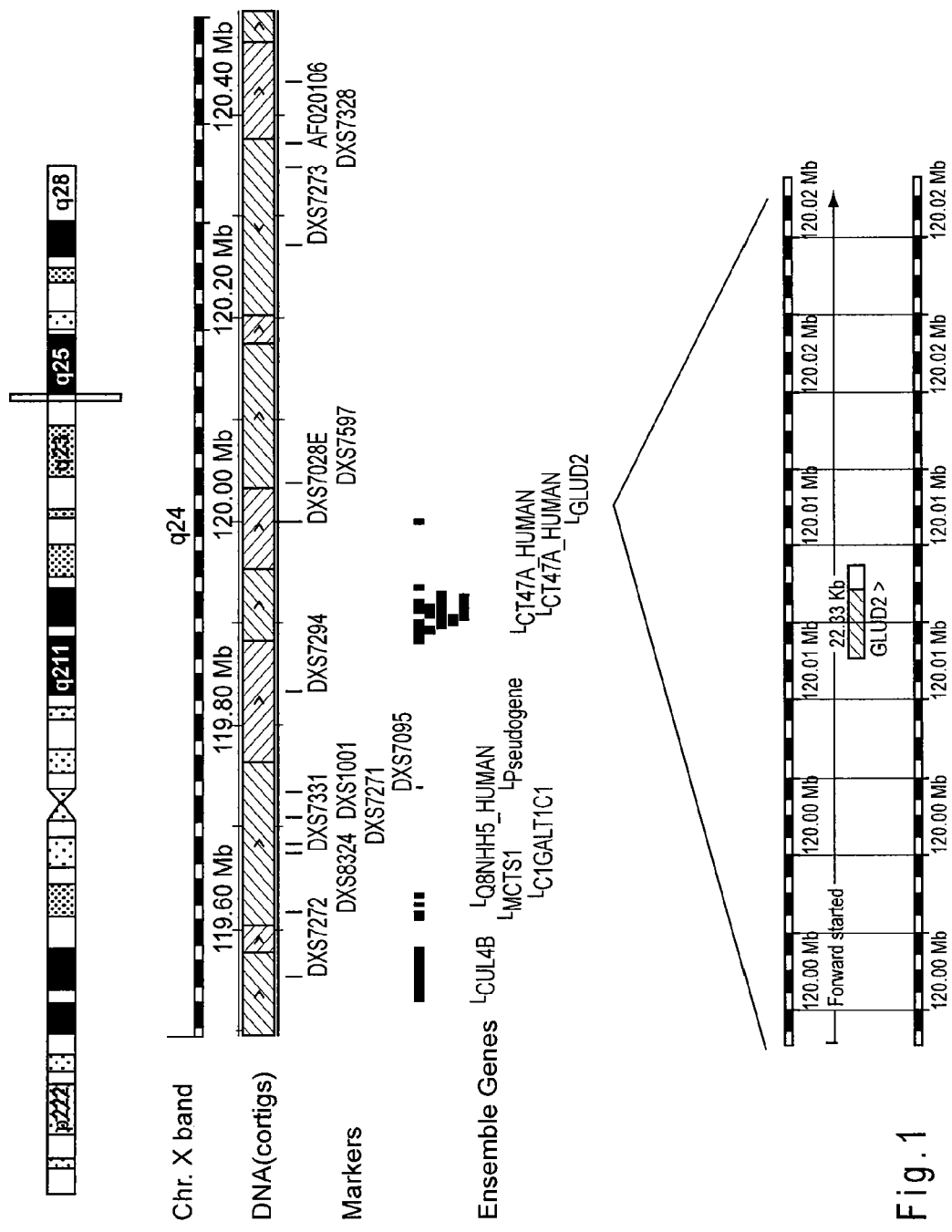
FIG. 1 is a view of chromosome X containing the GLUD2 gene (Xq24-q25) and the environment of the GLUD2 2.33 Kb transcript surrounded by various genes.

The following illustrates a gene polymorphism in the GLUD2 gene coding for an hGDH2 variant that was previously unknown in the art to be associated with neurodegenerative diseases. Accordingly, disclosed herein are novel compositions and methods of detecting and using the GLUD2 gene polymorphism and hGDH2 variant disclosed herein. The polymorphism disclosed herein is useful for evaluating neurodegenerative disorders and for treating neurodegenerative disorders such as Parkinson's disease, by, for example, retarding the onset of disease or slowing disease progression.

Methods of treatment illustrated herein include but are not limited to using agents that are specific inhibitors of hGDH2 and hGDH2 variants. Specific inhibitors may include steroid hormones or potent synthetic analogs of these compounds. Disclosed herein are the surprising discovery that steroid hormones inhibit potently hGDH2 and that this effect relates to the discovery that steroid hormones interact potently with GDH when the state of the activation of the enzyme is low, for example, when the enzyme is in a closed conformation. The difference between the sensitivity of estrogens for hGDH1 and hGDH2 may be due to the fact that hGDH1 maintains a relatively open baseline conformation (e.g., at baseline, hGDH1 displays about 40% of its maximal activity). By comparison, hGDH2 maintains at baseline a relatively closed conformation (e.g., displays about 4% to 8% of its maximal activity). Disclosed also is use of additional compounds that act by modifying the conformation of hGDH2 to potentiate the effect of the natural inhibitors.

The brain and central nervous system is made up of nerve cells called neurons. The primary method of information transfer within the brain is chemical signaling between neurons. Neurons contact other neurons in the brain and CNS at contact points called synapses. A neuron transmits information by way of a nerve impulse. When a nerve impulse arrives at a synapse, it releases neurotransmitters, which influence another cell, either in an inhibitory manner or an excitatory manner.

Glutamate is one of the principal neurotransmitters in the brain. Glutamate is an excitatory neurotransmitter. Nerve impulses trigger release of glutamate from the pre-synaptic cell. Post-synaptic cells have glutamate receptors which are activated when they bind glutamate. The excitatory action of glutamate is terminated by, among other things, uptake of the neurotransmitter into glial cells, such as astrocytes. Glial cells are non-neuronal cells that provide support and protection for neurons and participate in signal transmission in the brain and nervous system.

When glutamate concentrations around neurons become excessive, nerve cells may be overactivated which may lead to cell damage and cell death, a pathological process referred to as excitotoxicity. Excitotoxicity may be involved in spinal cord injury, stroke, traumatic brain injury and neurodegenerative diseases of the central nervous system (CNS) such as Multiple sclerosis, Alzheimer's disease, Amyotrophic lateral sclerosis (ALS), Parkinson's disease (PD), and Huntington's disease.

Abnormalities in glutamate metabolism have been reported in patients with neurodegenerative disorders, including PD, raising the possibility metabolic defects involving this amino acid might be operational. Glutamate is metabolized through various pathways, for example, by the enzyme glutamate dehydrogenase (GDH). GDH is a mitochondrial enzyme central to the metabolism of glutamate and also plays a role in cellular energetics. GDH is expressed at high levels in the liver, brain, kidney, pancreas, heart and lungs. Enzyme activity assays suggest that GDH may localize in both the glial cells (astrocytes) and neurons. GDH may also be present in the cytosol of oligodendrocytes. Oligodendrocytes are glial cells that may be involved in the pathogenesis of multiple sclerosis.

GDH is traditionally considered to be localized in the mitochondrial matrix but recent studies have shown that GDH may also be localized in the endoplasmic reticulum of cells. *Mastorodemos, V., Kotsamani D., Zaganas I., Arianoglou G., Laqtsoudis H. and Plaitakis A., Biochem. Cell. Biol.* 2009: 87:505-516 (incorporated herein by reference). The GDH that localizes to the endoplasmic reticulum retains the 53 amino acid N-terminal cleavable sequence, which is cleaved when the enzyme translocates into the mitochondrial matrix. Altered activities and increased thermal stability of glutamate dehydrogenase (GDH), a mitochondrial enzyme expressed in midbrain dopaminergic neurons have been described in patients with neurodegenerative disorders, including atypical PD.

GDH exists in at least two isoforms in the brain, hGDH1 and hGDH2. The hGDH1 isoform is widely expressed (housekeeping). The hGDH2 isoform is expressed in brain, testes, and in melanoma cells lines.

The two isoenzymes are encoded by structurally distinct genes designated GLUD1 and GLUD2, respectively. The GLUD1 gene contains introns and is located on chromosome 10q. The GLUD2 gene is an intronless gene that is located on the X chromosome. SEQ ID NO. 1 provides a nucleotide sequence for the human wild-type GLUD 2. SEQ ID NO. 2 provides an amino acid sequence for human wild-type GDH2. The isoenzymes share approximately 97% amino acid sequence homology. Both GDH1 and GDH2 are hexameric molecules composed of six identical subunits. FIG. 1 illustrates chromosome X containing the GLUD2 gene (Xq24-q25) and the environment of the GLUD2 2.33 Kb transcript surrounded by various genes.

The activity of each may be allosterically regulated by structurally diverse compounds. Both enzymes are allosterically activated by ADP and L-leucine. Activation of GDH leads to a flux of glutamate.

The isoenzymes differ in their basal state activity and in allosteric inhibition. For example, hGDH1 is catalytically active in its basal state. GTP inhibits hGDH1 activity. By contrast, even in the absence of GTP, hGDH2 assumes a basal conformational state associated with little catalytic activity. The activity of hGDH2 is not inhibited by GTP.

The difference in allosteric inhibition of the two isozymes may represent an evolutionary adaptation for the metabolism of the glutamate neurotransmitter. There is evidence that the human the GLUD1 gene (located on chromosome 10) has been retro-posed to the X chromosome, where it gave rise to the intronless GLUD2 gene through random polymorphisms and natural selection.

The GLUD2 gene might have adapted to the particular needs of the nervous system where it is specifically expressed. As GTP levels are generally higher in brain than in other tissues, GTP may not be a suitable modulator for GDH activity in neural tissue. Instead of being regulated by GTP, the hGDH2 may have developed a unique molecular mechanism that permits enzyme regulation without the allosteric inhibitor (GTP). The hGDH2 enzyme assumes, even in the absence of GTP, a closed conformation associated with a low-rate catalytic activity, but remains responsive to activation by ADP and/or L-leucine.

A genetic contribution to the pathogenesis of neurodegenerative disorders, such as PD, has been inferred from the increased prevalence of PD in incidence in families. However, to this date no sequence variation in the GLUD1 gene that encodes the widely expressed hGDH1 has been identified.

Figure 2:
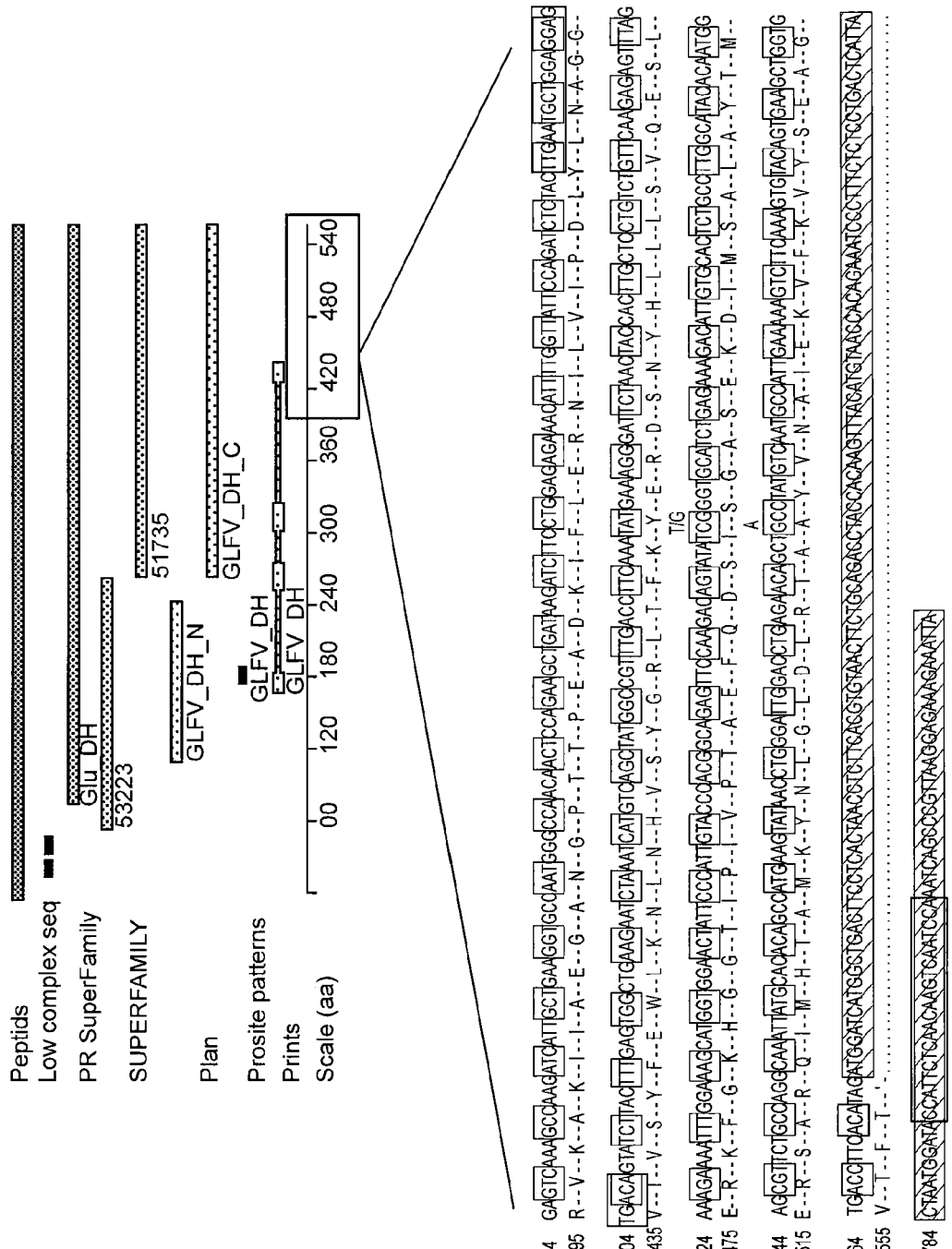
FIG. 2 is the GLUD2 gene coding for the human housekeeping GDH is composed of 558 residues. The figure shows all the functional domains of the protein (Glu/Leu/Phe/Val dehydrogenase amino- and carboxy-terminals and dimerisation region).

I have discovered a novel and previously unknown to be associated with human disorders single nucleotide polymorphism (SNP) in the coding region of the GLUD2 gene that correlates with the incidence of PD. The wild type (normal) GLUD2 gene is shown in FIG. 2 and disclosed in SEQ. ID. NO. 1. The SNP discovered has a substitution of guanine for thymine at nucleic acid position 1492, which is position 1569 in SEQ ID NO:1. SEQ. ID. NO. 3 is the identical nucleotide sequence called out in FIG. 2. SEQ. ID. NO. 3 represents a smaller region of SEQ ID NO. 1. Specifically, SEQ ID NO. 3 represents nucleotides 1261 through nucleotide 1920 of SEQ ID NO 1. Nucleic acid position 1492 discussed herein is represented by position 309 in SEQ ID NO. 3. The variant GLUD2 protein produced by that SNP incorporates the amino acid Alanine in the 445th position of the mature GLUD2 sequence (e.g., the GLUD2 sequence without the 53 N-terminal amino acids mitochondrial target sequence), represented as position 498 in SEQ. ID. NO. 2, in lieu of the amino acid serine that occupies that position in the normal hGDH2 protein. Ser445Ala refers to the mature amino acid sequence, which lacks 53 N-terminal amino acids (e.g., mitochondrial target sequence) that is removed upon import of the protein in the mitochondria. The numbering of SEQ. ID. NO. 2 includes the target sequence, thus Ser445Ala becomes Ser498Ala (as shown in FIG. 2 and SEQ. ID. NO. 2). The nucleotide sequence of the section of GLUD2 as illustrated with the rectangular box in FIG. 2 is shown as SEQ ID NO:3. The amino acid sequence of the section of GLUD2 as illustrated with the rectangular box in FIG. 2 is shown as SEQ ID NO:4 (Arg395 from FIG. 2 becomes Arg 1 in SEQ ID NO 4). The variant GLUD 2 protein produced by the T1569G replacement in SEQ. ID. NO. 1 is illustrated as a Ser104Ala mutation to SEQ. ID. NO. 4. Throughout the rest of this specification, reference to Ser445Ala is equivalent to a Ser498Ala to SEQ. ID. NO. 2 and a Ser104Ala to SEQ. ID. NO. 4.

The novel human GLUD2 gene is predominantly expressed in neural and testicular tissues, encoding hGDH2, an isoenzyme that shows a distinct regulation pattern. GLUD2 is also expressed in melanoma cells lines. Thus, while the activity of hGDH1 is controlled by GTP inhibition ($IC_{50}$=0.1-0.3 µM), hGDH2 is resistant to this compound ($IC_{50}$>200 µM) as a result of replacement of Gly456 by Ala (Zaganas and Plaitakis, 2002). Also, hGDH2 maintains a characteristic low basal activity (4-8% of maximal capacity) (Plaitakis et al., 2000), resulting from the evolutionary substitution of Ser for Arg443Ser that is thought to confer a closed conformation (Zaganas et al., 2002). As no negative modulators of hGDH2 activity are currently known, regulation of this enzyme is thought to be achieved by rising levels of the positive enzyme modulators ADP and L-leucine (Plaitakis et al., 2000).

In light of the above considerations, the effect of estrogens on human wild-type hGDH1 and hGDH2 was investigated, by obtaining in recombinant form by expression of the corresponding genes in Sf21 cells. Results unexpectedly revealed that estrogen interacted more potently with the neural and testicular tissue-specific isoenzyme (hGDH2) than with the widely expressed hGDH1. To elucidate the molecular mechanisms that render hGDH2 sensitive to estrogens, site-directed mutagenesis of the GLUD1 gene and the GLUD2 gene was performed. Results obtained and their implications on the biological function of these compounds are presented below.

Female hormones are known to exert multiple physiological actions by binding to estrogen receptors (ER) located in the plasma membrane of many cells. This binding triggers downstream signaling cascades, such as initiation of gene transcriptions that regulate cell growth, migration and other functions (Green and Simpkins, 2000). In addition to their effects on nuclear DNA processes, estrogens can also act via non-genomic mechanisms (Amantea et al., 2005). These include effects on calcium currents, oxidative stress and metabolic processes (Ba et al., 2004; Goodman et al., 1996). With respect to the latter, estrogens are thought to influence metabolism either by acting directly on metabolic enzymes (McEnery and Pederson, 1986; McEnery et al., 1989) or by modifying the transcription of such proteins (Ropero et al., 2006).

While glutamate dehydrogenase was the first metabolic enzyme shown to be inhibited by steroid hormones (Yielding and Tomkins, 1960), these direct effects were observed at estrogen concentrations higher than those expected to occur physiologically in mammalian tissues. However, previous studies that tested these estrogen effects employed GDH purified from bovine liver that expresses the single GLUD gene (GLUD1 in the human) present in all mammals. On the other hand, humans and great apes have acquired a second GDH-specific gene (GLUD2), thought to have emerged through a duplication event (transposition) (Shashidharan et al., 1994) that might have occurred <23 million years ago (Burki and Kaessmann, 2004).

DEFINITIONS

Nucleic acid molecules may be double-stranded molecules and that reference to a particular site on one strand refers, as well, to the corresponding site on a complementary strand. In defining a SNP position, SNP allele, or nucleotide sequence, reference to an adenine, thymine (uridine), cytosine, or guanine at a particular site on one strand of a nucleic acid molecule also defines the thymine (uridine), adenine, guanine, or cytosine (respectively) at the corresponding site on a complementary strand of the nucleic acid molecule. Thus, reference may be made to either strand in order to refer to a particular SNP position, SNP allele, or nucleotide sequence. Probes and primers may be designed to hybridize to either strand and SNP genotyping methods disclosed herein may generally target either strand. Throughout the specification, in identifying a SNP position, reference is generally made to the protein-encoding strand, only for the purpose of convenience.

Isolated Nucleic Acid Molecules.

The present disclosure provides isolated nucleic acid molecules that contain SNPs resulting in T1492G substitution. Position 1 of SEQ ID NO 1 begins 77 base pairs before the coding region, therefore, position 1492 is position 1569 of SEQ ID NO 1, thus the substitution according to SEQ ID NO 1 is T1569G and position 1492 is position 309 of SEQ. ID. NO. 3, thus the substitution according to SEQ. ID. NO. 3 is T309G;). Throughout the rest of this specification, reference to T1492G is equivalent to T1569G in SEQ ID NO 1 and T309G in SEQ. ID. NO. 3. Isolated nucleic acid molecules containing one or more SNPs may be interchangeably referred to throughout the present text as "SNP-containing nucleic acid molecules." Isolated nucleic acid molecules may optionally encode a full-length variant protein or fragment thereof. The isolated nucleic acid molecules presently disclosed also include probes and primers (which are described in greater detail below in the section entitled "SNP Detection Reagents"), which may be used for assaying the disclosed SNPs, and isolated full-length genes, transcripts, cDNA molecules, and fragments thereof, which may be used for such purposes as expressing an encoded protein.

An isolated nucleic acid molecule generally may be one that contains the disclosed SNP or one that hybridizes to such molecule such as a nucleic acid with a complementary sequence, and is separated from most other nucleic acids present in the natural source of the nucleic acid molecule. Moreover, an isolated nucleic acid molecule, such as a cDNA molecule containing the disclosed SNP, may be substantially free of other cellular material, or culture medium when produced by recombinant techniques, or chemical precursors or other chemicals when chemically synthesized. A nucleic acid molecule can be fused to other coding or regulatory sequences and still be considered isolated. Nucleic acid molecules present in non-human transgenic animals, which do not naturally occur in the animal, may also be considered isolated. For example, recombinant DNA molecules contained in a vector may be considered isolated. Further examples of isolated DNA molecules include recombinant DNA molecules maintained in heterologous host cells, and purified (partially or substantially) DNA molecules in solution. Isolated RNA molecules include in vivo or in vitro RNA transcripts of the isolated SNP-containing DNA molecules. Isolated nucleic acid molecules further include such molecules produced synthetically.

An isolated SNP-containing nucleic acid molecule can comprise, for example, a full-length gene or transcript, such as a gene isolated from genomic DNA (e.g., by cloning or PCR amplification), a cDNA molecule, or an mRNA transcript molecule. Furthermore, fragments of such full-length genes and transcripts that contain one or more SNPs disclosed herein are also encompassed, and such fragments may be used, for example, to express any part of a protein, such as a particular functional domain or an antigenic epitope.

Thus, also encompassed are fragments of the nucleic acid sequences encompassing the SNPs disclosed herein, contiguous nucleotide sequence at least about 8 or more nucleotides, alternatively at least about 12 or more nucleotides, and alternatively at least about 16 or more nucleotides. Further, a fragment could comprise at least about 15, 18, 20, 22, 25, 30, 40, 50, 60, 100, 250 or 500 (or any other number in-between) nucleotides in length. The length of the fragment will be based on its intended use. For example, the fragment can encode epitope-bearing regions of a variant peptide or regions of a variant peptide that differ from the normal/wild-type protein, or can be useful as a polynucleotide probe or primer. Such fragments can be isolated using all or part of the nucleotide sequences provided in FIG. 2 (the call out of which is represented in SEQ. ID. NO. 3) for the synthesis of a polynucleotide probe. A labeled probe can then be used, for example, to screen a cDNA library, genomic DNA library, or mRNA to isolate nucleic acid corresponding to the coding region. Further, primers can be used in amplification reactions, such as for purposes of assaying one or more SNPs sites or for cloning specific regions of a gene.

An isolated nucleic acid molecule as herein disclosed further encompasses a SNP-containing polynucleotide that is the product of any one of a variety of nucleic acid amplification methods, which are used to increase the copy numbers of a polynucleotide of interest in a nucleic acid sample. Such amplification methods may include but are not limited to, polymerase chain reaction (PCR) (U.S. Pat. Nos. 4,683,195; and 4,683,202; PCR Technology: Principles and Applications for DNA Amplification, ed. H. A. Erlich, Freeman Press, NY, N.Y., 1992), ligase chain reaction (LCR) (Wu and Wallace, Genomics 4:560, 1989; Landegren et al., Science 241:1077, 1988), strand displacement amplification (SDA) (U.S. Pat. Nos. 5,270,184; and 5,422,252), transcription-mediated amplification (TMA) (U.S. Pat. No. 5,399,491), linked linear amplification (LLA) (U.S. Pat. No. 6,027,923), and the like, and isothermal amplification methods such as nucleic acid sequence based amplification (NASBA), and self-sustained sequence replication (Guatelli et al., Proc. Natl. Acad. Sci. USA 87: 1874, 1990). All citations incorporated by reference herein. Based on such methodologies, primers may be designed in any suitable regions 5' and 3' to a SNP disclosed herein. Such primers may be used to amplify DNA of any length so long that it contains the SNP of interest in its sequence.

An amplified polynucleotide may be a SNP-containing nucleic acid molecule whose amount has been increased at least two fold by any nucleic acid amplification method performed in vitro as compared to its starting amount in a test sample. An amplified polynucleotide may be the result of at least ten fold, fifty fold, one hundred fold, one thousand fold, or even ten thousand fold increase as compared to its starting amount in a test sample. In a typical PCR amplification, a polynucleotide of interest is often amplified at least fifty thousand fold in amount over the unamplified genomic DNA, but the precise amount of amplification needed for an assay depends on the sensitivity of the subsequent detection method used. It is understood that irrespective of the length of an amplified polynucleotide, a SNP of interest may be located anywhere along its sequence.

Further illustrated and provided are nucleic acid molecules that comprise any of the nucleotide sequences encoding the T1492G polymorphism. Nucleic acid molecules comprise a nucleotide sequence when the nucleotide sequence is at least part of the final nucleotide sequence of the nucleic acid molecule. In such a fashion, the nucleic acid molecule can be only the nucleotide sequence or have additional nucleotide residues, such as residues that are naturally associated with it or heterologous nucleotide sequences. Such a nucleic acid molecule can have one to a few additional nucleotides or can comprise many more additional nucleotides. A brief description of how various types of these nucleic acid molecules can be readily made and isolated is provided below (Sambrook and Russell, 2000, Molecular Cloning: A Laboratory Manual, Cold Spring Harbor Press, NY), incorporated by reference herein.

Isolated nucleic acid molecules can be in the form of RNA, such as mRNA, or in the form DNA, including cDNA and genomic DNA, which may be obtained, for example, by molecular cloning or produced by chemical synthetic techniques or by a combination thereof (Sambrook and Russell, 2000, Molecular Cloning: A Laboratory Manual, Cold Spring Harbor Press, NY). Furthermore, isolated nucleic acid molecules, particularly SNP detection reagents such as probes and primers, can also be partially or completely in the form of one or more types of nucleic acid analogs, such as peptide nucleic acid (PNA) (U.S. Pat. Nos. 5,539,082; 5,527,675; 5,623,049; 5,714,331). The nucleic acid, especially DNA, can be double-stranded or single-stranded. Single-stranded nucleic acid can be the coding strand (sense strand) or the complementary non-coding strand (anti-sense strand). DNA, RNA, or PNA segments can be assembled, for example, from fragments of the human genome (in the case of DNA or RNA) or single nucleotides, short oligonucleotide linkers, or from a series of oligonucleotides, to provide a synthetic nucleic acid molecule. Nucleic acid molecules can be readily synthesized using the sequences provided herein as a reference (see, e.g., Corey, "Peptide nucleic acids: expanding the scope of nucleic acid recognition," Trends Biotechnol. 1997 June; 15(6):224-9, and Hyrup et al., "Peptide nucleic acids (PNA): synthesis, properties and potential applications," Bioorg. Med. Chem. 1996 January; 4(1):5-23). Furthermore, large-scale automated oligonucleotide/PNA synthesis (including synthesis on an array or bead surface or other solid support) can readily be accomplished using commercially available nucleic acid synthesizers, such as the Applied Biosystems (Foster City, Calif.) 3900 High-Throughput DNA Synthesizer or Expedite 8909 Nucleic Acid Synthesis System, and the sequence information provided herein. All citations incorporated by reference herein.

The present disclosure encompasses nucleic acid analogs that contain modified, synthetic, or non-naturally occurring nucleotides or structural elements or other alternative/modified nucleic acid chemistries known in the art. Such nucleic acid analogs are useful, for example, as detection reagents (e.g., primers/probes) for detecting one or more SNPs. Furthermore, kits/systems (such as beads, arrays, etc.) that include these analogs are also encompassed. For example, PNA oligomers that are based on the polymorphic sequences are specifically contemplated. PNA oligomers are analogs of DNA in which the phosphate backbone is replaced with a peptide-like backbone (Lagriffoul et al., Bioorganic & Medicinal Chemistry Letters, 4: 1081-1082 (1994), Petersen et al., Bioorganic & Medicinal Chemistry Letters, 6:793-796 (1996), Kumar et al., Organic Letters 3(9):1269-1272 (2001), WO96/04000). All citations incorporated by reference herein. PNA hybridizes to complementary RNA or DNA with higher affinity and specificity than conventional oligonucleotides and oligonucleotide analogs. The properties of PNA enable novel molecular biology and biochemistry applications unachievable with traditional oligonucleotides and peptides.

Diagnostic and Evaluative Uses

SNP Detection Reagents

Disclosed herein is a method of detecting PD by identifying this polymorphism in DNA or mRNA (or on other nucleic acid sequences, such as cDNA, developed there from) contained in tissue, blood or other biological samples. The polymorphism can be detected in any manner conventionally known in the art, e.g., via directly sequencing the nucleotide sequences contained in the samples, though it is preferably detected by, first, amplifying those sequences, e.g., via polymerase chain reaction (PCR).

Alternatively, or in addition, the disease can be detected by identification of the variant protein in tissue, blood or other biological samples. Such diagnosis or even prediction can also be made by identifying the polymorphism or variant in samples taken from kindred or other relatives of a human being. This can be helpful, for example, in determining whether offspring are likely to be genetically predisposed to the condition, even though it has not expressed itself in parents.

The GLUD2 gene coding for hGDH2 is composed of approximately 558 residues. FIG. 2 shows the functional domains of the protein (Glu/Leu/Phe/Val dehydrogenase amino- and carboxy-terminals and dimerisation region). FIG. 2 also shows one example of primers that may be used to amplify a region of 527 bp. The example is meant to be illustrative not limiting. Other primers are contemplated. PCR amplification may be performed, for example but not limited to, in a total volume of 25 μL, containing 100 ng of genomic DNA, 5 pmol of each primer, 200 μM of each dNTP, 1×PCR buffer, and 2.5 U of Taq DNA polymerase. The Ser445Ala variant may be determined using RFLP analysis. In this example, the 1492T→G polymorphism created a restriction site for the enzyme AciI (New England Biolabs, Inc) and the resulting 204 bp and 323 bp sub-fragments were visualised on a 3% agarose gel. Putative carriers of the 1492T→G variant may be sequenced to confirm their genotype.

In one aspect, the SNPs disclosed herein can be used for the design of SNP detection reagents. A SNP detection reagent may be a reagent that specifically detects a specific target SNP position disclosed herein, and that is preferably specific for a particular nucleotide (allele) of the target SNP position (i.e., the detection reagent preferably can differentiate between different alternative nucleotides at a target SNP position, thereby allowing the identity of the nucleotide present at the target SNP position to be determined). Typically, such detection reagent hybridizes to a target SNP-containing nucleic acid molecule by complementary base-pairing in a sequence specific manner, and discriminates the target variant sequence from other nucleic acid sequences such as an art-known form in a test sample. An example of a detection reagent is a probe that hybridizes to a target nucleic acid containing one or more of the SNPs. For example, such a probe can differentiate between nucleic acids having a particular nucleotide (allele) at a target SNP position from other nucleic acids that have a different nucleotide at the same target SNP position. In addition, a detection reagent may hybridize to a specific region 5' and/or 3' to a SNP position, particularly a region corresponding to the context sequences. Another example of a detection reagent is a primer which acts as an initiation point of nucleotide extension along a complementary strand of a target polynucleotide. The SNP sequence information provided herein is also useful for designing primers, e.g. allele-specific primers, to amplify (e.g., using PCR) any SNP herein disclosed.

A SNP detection reagent may be an isolated or synthetic DNA or RNA polynucleotide probe or primer or PNA oligomer, or a combination of DNA, RNA and/or PNA, that hybridizes to a segment of a target nucleic acid molecule containing a SNP identified in FIG. 2 (the call-out of which is also represented as SEQ ID NO 3). A detection reagent in the form of a polynucleotide may optionally contain modified base analogs, intercalators or minor groove binders. Multiple detection reagents such as probes may be, for example, affixed to a solid support (e.g., arrays or beads) or supplied in solution (e.g., probe/primer sets for enzymatic reactions such as PCR, RT-PCR, TaqMan assays, or primer-extension reactions) to form a SNP detection kit.

A probe or primer typically is a substantially purified oligonucleotide or PNA oligomer. Such oligonucleotide typically comprises a region of complementary nucleotide sequence that hybridizes under stringent conditions to at least about 8, 10, 12, 16, 18, 20, 22, 25, 30, 40, 50, 60, 100 (or any other number in-between) or more consecutive nucleotides in a target nucleic acid molecule. Depending on the particular assay, the consecutive nucleotides can either include the target SNP position, or be a specific region in close enough proximity 5' and/or 3' to the SNP position to carry out the desired assay.

Primers and probes may be directly useful as reagents for genotyping the SNPs disclosed herein, and can be incorporated into any kit/system format.

In order to produce a probe or primer specific for a target SNP-containing sequence, the gene/transcript and/or context sequence surrounding the SNP of interest is typically examined using a computer algorithm which starts at the 5' or at the 3' end of the nucleotide sequence. Typical algorithms will then identify oligomers of defined length that are unique to the gene/SNP context sequence, have a GC content within a range suitable for hybridization, lack predicted secondary structure that may interfere with hybridization, and/or possess other desired characteristics or that lack other undesired characteristics.

The maximal length of a probe may be as long as the target sequence to be detected, depending on the type of assay in which it is employed, however, it may be typically less than about 50, 60, 65, or 70 nucleotides in length. In the case of a primer, it may be typically less than about 30 nucleotides in length.

However, in nucleic acid arrays and other embodiments in which probes are affixed to a substrate, the probes may be longer, such as on the order of 30-70, 75, 80, 90, 100, or more nucleotides in length (see the section below entitled "SNP Detection Kits and Systems").

For analyzing SNPs, it may be appropriate to use oligonucleotides specific for alternative SNP alleles. Such oligonucleotides which detect single nucleotide variations in target sequences may be referred to by such terms as "allele-specific oligonucleotides," "allele-specific probes," or "allele-specific primers." The design and use of allele-specific probes for analyzing polymorphisms is described in, e.g., Mutation Detection A Practical Approach, ed. Cotton et al. Oxford University Press, 1998; Saiki et al., Nature 324, 163-166 (1986); Dattagupta, EP235,726; and Saiki, WO 89/11548. All citations incorporated by reference herein.

While the design of each allele-specific primer or probe depends on variables such as the precise composition of the nucleotide sequences flanking a SNP position in a target nucleic acid molecule, and the length of the primer or probe, another factor in the use of primers and probes is the stringency of the condition under which the hybridization between the probe or primer and the target sequence is performed. Higher stringency conditions utilize buffers with lower ionic strength and/or a higher reaction temperature, and tend to require a more perfect match between probe/primer and a target sequence in order to form a stable duplex. If the stringency is too high, however, hybridization may not occur at all. In contrast, lower stringency conditions utilize buffers with higher ionic strength and/or a lower reaction temperature, and permit the formation of stable duplexes with more mismatched bases between a probe/primer and a target sequence. By way of example and not limitation, exemplary conditions for high stringency hybridization conditions using an allele-specific probe are as follows: Prehybridization with a solution containing 5× standard saline phosphate EDTA (SSPE), 0.5% NaDodSO4 (SDS) at 55° C., and incubating probe with target nucleic acid molecules in the same solution at the same temperature, followed by washing with a solution containing 2×SSPE, and 0.1% SDS at 55° C. or room temperature.

Moderate stringency hybridization conditions may be used for allele-specific primer extension reactions with a solution containing, e.g., about 50 mM KCl at about 46° C. Alternatively, the reaction may be carried out at an elevated temperature such as 60° C. Alternatively or additionally, a moderately stringent hybridization condition suitable for oligonucleotide ligation assay (OLA) reactions wherein two probes are ligated if they are completely complementary to the target sequence may utilize a solution of about 100 mM KCl at a temperature of 46° C.

In a hybridization-based assay, allele-specific probes can be designed that hybridize to a segment of target DNA from one individual but do not hybridize to the corresponding segment from another individual due to the presence of different polymorphic forms (e.g., alternative SNP alleles/nucleotides) in the respective DNA segments from the two individuals. Hybridization conditions should be sufficiently stringent that there is a significant detectable difference in hybridization intensity between alleles, and preferably an essentially binary response, whereby a probe hybridizes to only one of the alleles or significantly more strongly to one allele. While a probe may be designed to hybridize to a target sequence that contains a SNP site such that the SNP site aligns anywhere along the sequence of the probe, the probe is preferably designed to hybridize to a segment of the target sequence such that the SNP site aligns with a central position of the probe (e.g., a position within the probe that is at least three nucleotides from either end of the probe). This design of probe generally achieves good discrimination in hybridization between different allelic forms.

A probe or primer may be designed to hybridize to a segment of target DNA such that the SNP aligns with either the 5' end or the 3' end of the probe or primer.

Oligonucleotide probes and primers may be prepared chemical synthetic methods that include, but are limited to, the phosphotriester method described by Narang et al., 1979, Methods in Enzymology 68:90; the phosphodiester method described by Brown et al., 1979, Methods in Enzymology 68:109, the diethylphosphoamidate method described by Beaucage et al., 1981, Tetrahedron Letters 22:1859; and the solid support method described in U.S. Pat. No. 4,458,066. All citations incorporated by reference herein.

Allele-specific probes are often used in pairs (or, less commonly, in sets of 3 or 4, such as if a SNP position is known to have 3 or 4 alleles, respectively, or to assay both strands of a nucleic acid molecule for a target SNP allele), and such pairs may be identical except for a one nucleotide mismatch that represents the allelic variants at the SNP position. Commonly, one member of a pair perfectly matches a reference form of a target sequence that has a more common SNP allele (i.e., the allele that is more frequent in the target population) and the other member of the pair perfectly matches a form of the target sequence that has a less common SNP allele (i.e., the allele that is rarer in the target population). In the case of an array, multiple pairs of probes can be immobilized on the same support for simultaneous analysis of multiple different polymorphisms.

In one type of PCR-based assay, an allele-specific primer hybridizes to a region on a target nucleic acid molecule that overlaps a SNP position and only primes amplification of an allelic form to which the primer exhibits perfect complementarity (Gibbs, 1989, Nucleic Acid Res. 17:2427-2448). All citations incorporated by reference herein. Typically, the primer's 3'-most nucleotide is aligned with and complementary to the SNP position of the target nucleic acid molecule. This primer may be used in conjunction with a second primer that hybridizes at a distal site. Amplification may proceed from the two primers, producing a detectable product that indicates which allelic form is present in the test sample. A control is usually performed with a second pair of primers, one of which shows a single base mismatch at the polymorphic site and the other of which exhibits perfect complementarity to a distal site. The single-base mismatch prevents amplification or substantially reduces amplification efficiency, so that either no detectable product is formed or it is formed in lower amounts or at a slower pace. The method generally works most effectively when the mismatch is at the 3'-most position of the oligonucleotide (i.e., the 3'-most position of the oligonucleotide aligns with the target SNP position) because this position is most destabilizing to elongation from the primer (see, e.g., WO 93/22456, incorporated by reference herein). This PCR-based assay can be utilized as part of the TaqMan assay, described below.

A SNP detection reagent as herein disclosed may be labeled with a fluorogenic reporter dye that emits a detectable signal. The reporter dye may be a fluorescent dye, or any reporter dye that can be attached to a detection reagent such as an oligonucleotide probe or primer. Such dyes include, but are not limited to, Acridine, AMCA, BODIPY, Cascade Blue, Cy2, Cy3, Cy5, Cy7, Dabcyl, Edans, Eosin, Erythrosin, Fluorescein, 6-Fam, Tet, Joe, Hex, Oregon Green, Rhodamine, Rhodol Green, Tamra, Rox, and Texas Red.

The detection reagent may be further labeled with a quencher dye such as Tamra, especially when the reagent is used as a self-quenching probe such as a TaqMan (U.S. Pat. Nos. 5,210,015 and 5,538,848) or Molecular Beacon probe (U.S. Pat. Nos. 5,118,801 and 5,312,728), or other stemless or linear beacon probe (Livak et al., 1995, PCR Method Appl. 4:357-362; Tyagi et al., 1996, Nature Biotechnology 14: 303-308; Nazarenko et al., 1997, Nucl. Acids Res. 25:2516-2521; U.S. Pat. Nos. 5,866,336 and 6,117,635. All citations incorporated by reference herein.

The detection reagents may also contain other labels, including but not limited to, biotin for streptavidin binding, hapten for antibody binding, and oligonucleotide for binding to another complementary oligonucleotide such as pairs of zip codes.

Additionally or alternatively there may be reagents that do not contain (or that are complementary to) a SNP nucleotide identified herein but that are used to assay one or more SNPs disclosed herein. For example, primers that flank, but do not hybridize directly to a target SNP position provided herein are useful in primer extension reactions in which the primers hybridize to a region adjacent to the target SNP position (i.e., within one or more nucleotides from the target SNP site). During the primer extension reaction, a primer is typically not able to extend past a target SNP site if a particular nucleotide (allele) is present at that target SNP site, and the primer extension product can readily be detected in order to determine which SNP allele is present at the target SNP site. For example, particular ddNTPs are typically used in the primer extension reaction to terminate primer extension once a ddNTP is incorporated into the extension product (a primer extension product which includes a ddNTP at the 3'-most end of the primer extension product, and in which the ddNTP corresponds to a SNP disclosed herein, is a composition that is encompassed). Thus, reagents that bind to a nucleic acid molecule in a region adjacent to a SNP site, even though the bound sequences do not necessarily include the SNP site itself, are also encompassed.

SNP Detection Kits and Systems

Based on the SNP and associated sequence information disclosed herein, detection reagents can be developed and used to assay any SNP disclosed herein individually or in combination, and such detection reagents can be readily incorporated into one of the established kit or system formats. The terms "kits" and "systems," as used herein in the context of SNP detection reagents, are intended to refer to such things as combinations of multiple SNP detection reagents, or one or more SNP detection reagents in combination with one or more other types of elements or components (e.g., other types of biochemical reagents, containers, packages such as packaging intended for commercial sale, substrates to which SNP detection reagents are attached, electronic hardware components, etc.).

Accordingly, provided are SNP detection kits and systems, including but not limited to, packaged probe and primer sets (e.g., TaqMan probe/primer sets), arrays/microarrays of nucleic acid molecules, and beads that contain one or more probes, primers, or other detection reagents for detecting one or more SNPs herein disclosed. The kits/systems can optionally include various electronic hardware components; for example, arrays ("DNA chips") and microfluidic systems ("lab-on-a-chip" systems) provided by various manufacturers typically comprise hardware components. Other kits/systems (e.g., probe/primer sets) may not include electronic hardware components, but may be comprised of, for example, one or more SNP detection reagents (along with, optionally, other biochemical reagents) packaged in one or more containers.

SNP detection kits/systems may contain, for example, one or more probes, or pairs of probes, that hybridize to a nucleic acid molecule at or near each target SNP position. Multiple pairs of allele-specific probes may be included in the kit/system to simultaneously assay large numbers of SNPs, at least one of which is a SNP herein disclosed. In some kits/systems, the allele-specific probes are immobilized to a substrate such as an array or bead. For example, the same substrate can comprise allele-specific probes for detecting one or more SNPs, including the SNPs shown in FIG. 2.

Arrays, microarrays, and DNA chips may be used herein interchangeably to refer to an array of distinct polynucleotides affixed to a substrate, such as glass, plastic, paper, nylon or other type of membrane, filter, chip, or any other suitable solid support. The polynucleotides can be synthesized directly on the substrate, or synthesized separate from the substrate and then affixed to the substrate. In one example, the microarray may be prepared and used according to the methods described in U.S. Pat. No. 5,837,832, Chee et al., PCT application WO95/11995 (Chee et al.), Lockhart, D. J. et al. (1996; Nat. Biotech. 14: 1675-1680) and Schena, M. et al. (1996; Proc. Natl. Acad. Sci. 93: 10614-10619), all of which are incorporated herein in their entirety by reference. In other examples, such arrays may be produced by the methods described by Brown et al., U.S. Pat. No. 5,807,522. All citations incorporated by reference herein.

Hybridization assays based on polynucleotide arrays rely on the differences in hybridization stability of the probes to perfectly matched and mismatched target sequence variants. For SNP genotyping, it is generally preferable that stringency conditions used in hybridization assays are high enough such that nucleic acid molecules that differ from one another at as little as a single SNP position can be differentiated (e.g., typical SNP hybridization assays are designed so that hybridization will occur only if one particular nucleotide is present at a SNP position, but will not occur if an alternative nucleotide is present at that SNP position). Such high stringency conditions may be preferable when using, for example, nucleic acid arrays of allele-specific probes for SNP detection. Such high stringency conditions are described in the preceding section can be found in, for example, Current Protocols in Molecular Biology, John Wiley & Sons, N.Y. (1989), 6.3.1-6.3.6. All citations incorporated by reference herein.

In other examples, the arrays may be used in conjunction with chemiluminescent detection technology. The following patents and patent applications, which are all hereby incorporated by reference, provide additional information pertaining to chemiluminescent detection: U.S. patent application Ser. Nos. 10/620,332 and 10/620,333 describe chemiluminescent approaches for microarray detection; U.S. Pat. Nos. 6,124,478, 6,107,024, 5,994,073, 5,981,768, 5,871,938, 5,843,681, 5,800,999, and 5,773,628 describe methods and compositions of dioxetane for performing chemiluminescent detection; and U.S. published application US2002/0110828 discloses methods and compositions for microarray controls. All citations incorporated by reference herein.

A nucleic acid array may comprise an array of probes of about 15-25 nucleotides in length. Alternatively or additionally, a nucleic acid array can comprise any number of probes, in which at least one probe is capable of detecting one or more SNPs disclosed in FIG. 2, and/or at least one probe comprises a fragment of one of the sequences selected from the group consisting of those disclosed in FIG. 2, the Sequence Listing NOS. 1-4, and sequences complementary thereto, said fragment comprising at least about 8 consecutive nucleotides, preferably 10, 12, 15, 16, 18, 20, more preferably 22, 25, 30, 40, 47, 50, 55, 60, 65, 70, 80, 90, 100, or more consecutive nucleotides (or any other number in-between) and containing (or being complementary to) a novel SNP allele disclosed in FIG. 2 (the call out of which is represented by SEQ ID NO 3). In some examples, the nucleotide complementary to the SNP site is within 5, 4, 3, 2, or 1 nucleotide from the center of the probe, more preferably at the center of said probe.

A polynucleotide probe can be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more polynucleotides, or any other number which lends itself to the efficient use of commercially available instrumentation.

Using such arrays or other kits/systems, the present disclosure provides methods of identifying the SNPs disclosed herein in a test sample. Such methods typically involve incubating a test sample of nucleic acids with an array comprising one or more probes corresponding to at least one SNP position of the disclosed herein, and assaying for binding of a nucleic acid from the test sample with one or more of the probes. Conditions for incubating a SNP detection reagent (or a kit/system that employs one or more such SNP detection reagents) with a test sample vary. Incubation conditions depend on such factors as the format employed in the assay, the detection methods employed, and the type and nature of the detection reagents used in the assay. Any one of the commonly available hybridization, amplification and array assay formats can readily be adapted to detect the SNPs disclosed herein.

A SNP detection kit/system may include components that are used to prepare nucleic acids from a test sample for the subsequent amplification and/or detection of a SNP-containing nucleic acid molecule. Such sample preparation components can be used to produce nucleic acid extracts (including DNA and/or RNA) from skin, biopsies, or tissue specimens. Methods of preparing nucleic acids may be readily adapted to obtain a sample that is compatible with the system utilized. Automated sample preparation systems for extracting nucleic acids from a test sample are commercially available, and examples are Qiagen's BioRobot 9600, Applied Biosystems' PRISM 6700, and Roche Molecular Systems'COBAS AmpliPrep System. All citations incorporated by reference herein.

Kits are provided for detecting a single nucleotide polymorphisms (SNP) in a nucleic acid. For example, kits for detecting a single nucleotide polymorphisms (SNP) in a nucleic acid, comprising the polynucleotide described above that are capable of detecting the presence or absence of the GDH2 T1492G polymorphism. Such kits may also contain a buffer, and an enzyme, such as a polymerase enzyme for primer extension.

Uses of Nucleic Acid Molecules

The nucleic acid molecules disclosed herein have a variety of uses, especially in the evaluation and treatment of neurodegenerative diseases such as PD. For example, the nucleic acid molecules are useful as hybridization probes, such as for genotyping SNPs in messenger RNA, transcript, cDNA, genomic DNA, amplified DNA or other nucleic acid molecules, and for isolating full-length cDNA and genomic clones encoding the variant peptides disclosed in FIG. 2 (SEQ ID NO. 2 representing a more complete peptide sequence and SEQ ID NO. 4 representing the peptide sequence disclosed in the call-out of FIG. 2) as well as their orthologs.

Probes can be used as part of a diagnostic test kit for identifying cells or tissues in which a variant protein is expressed, such as by measuring the level of a variant protein-encoding nucleic acid (e.g., mRNA) in a sample of cells from a subject or determining if a polynucleotide contains a SNP of interest.

Treatment

Further illustrated is the treatment of PD by detecting and remediating (e.g., via conventional gene therapy techniques) the genomic polymorphism either systemically or in the effected tissues. Alternatively, such treatment may be attained by application of appropriate medications, e.g., for blocking the polymorphic GDH active site, or clearance of the polymorphic GDH by treatment with antibodies specific for the polymorphism. Antibodies may also be developed to inhibit hGDH2 activity by blocking the polymorphic hGDH2 active site.

Steroid Treatment

A treatment may comprise the administration of a therapeutically effective amount of a composition containing one or more steroids. Steroids which may have a higher affinity for hGDH2 (or GLUD2) than hGDH1 (and therefore may specifically inhibit hGDH2, even in the presence of hGDH1) may be used alone or in combination with other compounds. Estrogens may inhibit hGDH2 with an affinity that is, e.g., about 20-fold higher than the affinity of estrogen for hGDH1. For example, estrogens or similar compounds may be used to specifically inhibit hGDH2 and, therefore, may be used to treat human disorders linked to deregulation of hGDH2. Estrogens or similar compounds may be particularly useful for treating disorders linked to deregulation of the Ser445Ala-hGDH2 enzyme associated with a gain of function polymorphism as described herein.

In addition to PD, the present disclosure may be applied to the diagnosis and/or treatment of other neurodegenerative disorders associated with excitotoxicity. The foregoing techniques can likewise be applied to other mammals that synthesize, utilize and/or metabolize glutamate in a manner similar to that of humans.

EXAMPLES AND METHODS

Example 1

Detection of GDH Polymorphism in Patients Suffering from Parkinson's Disease

The following illustrates a disease-predisposing alleles in the GLUD2 gene in patients affected by this disorder. Sequencing of the entire GLUD2 gene, including its promoter region, in PD patients and controls from Crete revealed that a rare polymorphism (T1492G), which results in substitution of Ser445 for Ala in the regulatory domain of the enzyme FIG. 3, was present in about 4% of the female subjects and about 2% of male individuals (Table 1). While the G allele frequency was comparable between PD patients (3.6%) and controls (3.4%), G-hemizygous males experienced disease onset 15 years earlier than patients with the other genotypes (Table 1). Gender, however, had no effect on age at onset or on age at diagnosis for PD patients with the T allele. Besides age, other phenotypic features such as the clinical type of PD (akinetic, tremorogenic or mixed) or the presence of a positive history showed no significant interaction with the Ser445Ala polymorphism.

TABLE 1

| A. Greek PD patients[a] | | | | | |
|---|---|---|---|---|---|
| | Males (Total N = 335) | | Females (Total N = 249) | | |
| | G | T | G/T | T/T | P value |
| Number of patients (Total = 584) | 12 | 323 | 18 | 231 | G versus G/T = 0.001 G versus T = 0.003 G versus T/T = 0.011 |
| Age at onset (mean years ± SD) | 54.6 ± 11.1 | 64.0 ± 10.7 | 67.7 ± 8.1 | 62.9 ± 11.0 | |
| B. North American PD patients | | | | | |
| | Males (N = 119) | | Females (N = 105) | | |
| | G | T | G/T | T/T | P value |
| Number of patients (N = 224) | 6 | 113 | 8 | 97 | G versus G/T = 0.049 G versus |

TABLE 1-continued

| | | | | | |
|---|---|---|---|---|---|
| Age at diagnosis (mean years ± SD) | 61.3 ± 15.7 | 67.4 ± 10.7 | 74.4 ± 5.8 | 68.7 ± 11.3 | T = 0.190 G versus T/T = 0.1321 |

*a*The first and the replication Greek study combined.

TABLE 2

| | Allele frequency (%) | | P value | $x^2$ | OR (95% CI) |
|---|---|---|---|---|---|
| | T | G | | | |
| Greek PD patients (n = 833) | 803 (96.4%) | 30 (3.6%) | 0.913 | 0.01 | 1.07 (0.61-1.87) |
| Greek controls (n = 799) | 772 (96.6%) | 27 (3.4%) | | | |
| North American PD patients (n = 329) | 315 (95.7%) | 14 (4.3%) | 0.599 | 0.28 | 1.57 (0.48-6.65) |
| North American controls (n = 145) | 141 (97.2%) | 4 (2.8%) | | | | n: number of chromosomes studied,
CI: Confidence Intervals n: number of chromosomes studied, CI: Confidence Intervals Subjects. The study consisted of 808 PD patients in total. Of these, 584 were from Greece and 224 from Central California. The Greek group encompassed 281 PD patients from Crete and 303 PD patients from Central Greece. PD patients from Crete were recruited from the Neurology Services of the University Hospital of Crete between 1997 and 2006. The PD patients from Central Greece and Peloponnese were recruited from the Neurology Services of the University Hospitals of Larissa and Patras according to the methods reported. The North American cohort was ascertained through a population-based procedure in Central California. When PD was encountered in more than one family member, only the index case was included, as members of the same kindred may share genetic polymorphisms. Controls were selected randomly from the local populations. These were individuals without a neurological disorder prior to or during the study and whose age was similar to that of the PD patients. Written consent was obtained from all participants according to protocols approved by the Institutional Review Boards.

Sequencing of the GLUD2 gene. Total genomic DNA was extracted from peripheral blood using the FlexiGene DNA kit (Qiagen Ltd) according to the manufacturer's instructions. Oligonucleotide primers were designed specifically to amplify the intronless GLUD2 gene, including its putative promoter. PCR amplification reaction mixture and thermal cycling conditions, as well as the oligonucleotide sequences are available upon request. The amplified products of PD patients were analysed by direct sequencing in an ABI Prism® 3100-direct automated genetic analyser (PE Applied Biosystems®) using Applied Biosystems BigDye™ Terminator v3.1 Cycle Sequencing kit and chromatograms were subsequently analysed using the software Sequencher™ v4.0.5 (Gene Codes Corporation) in order to determine the presence of any (known or novel) variations within this gene.

Genotyping of PD and control DNAs. Following the identification of the two aforementioned point variations leading to Gly35Arg and Ser445Ala substitutions, employed RFLP analysis was employed and/or the SnapShot assay to genotype PD and controls. Genotypic analyses of PD patients and controls were performed blindly using a pre-designed protocol. The presence of the detected DNA polymorphisms in a particular individual was confirmed by DNA sequencing.

Obtaining the T1492G-GLUD2 construct. Using genomic DNA from a male PD patient carrying the T1492G variant as a template, a 527 base pair segment of the GLUD2 gene was amplified by PCR. From this amplified segment, a 350 base pair fragment containing the T1492G change was cleaved using BsmI and BsrGI restriction endonucleases and inserted into a BsmI/BsrGI-digested GLUD2 cDNA cloned in pBSKII+ vector, replacing the corresponding region of the gene. Cloning of human GLUD2 and GLUD1 genes in pBSKII+ vector has been described elsewhere[15]

Example 2

Characterizing Protein Function of Variant hGDH2

Figure 6:
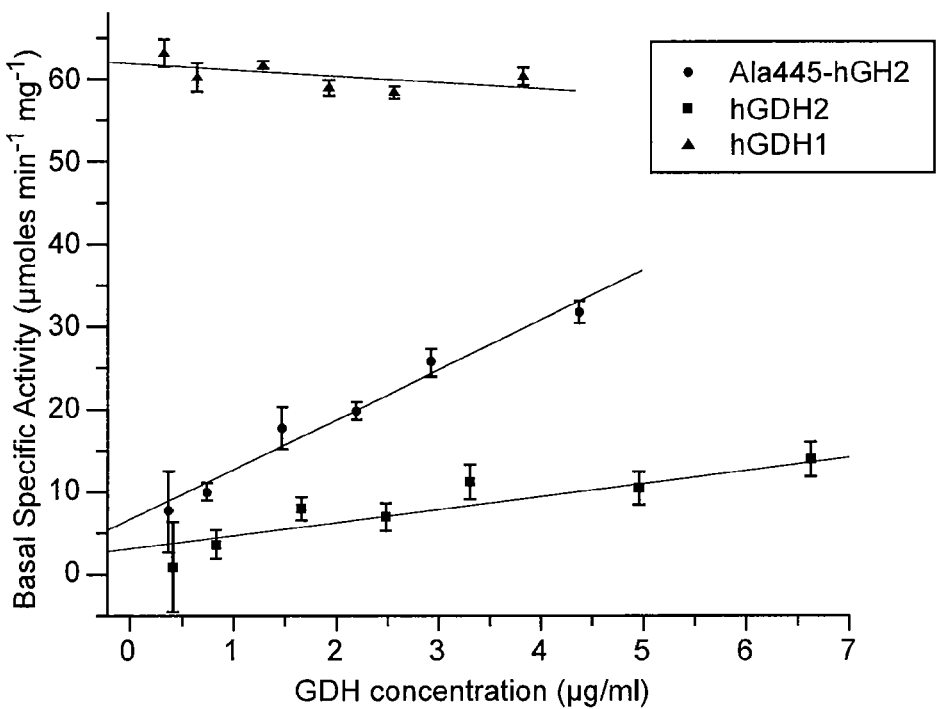
FIG. 6 is a chart representing Basal specific activity versus GDH concentration.

To investigate whether the Ser445Ala change modified the protein function of hGDH2, an Ala445-hGDH2 variant was obtained in recombinant form by expressing in Sf21 cells using the baculovirus expression system a GLUD2 cDNA with G instead of 1492T. Functional analysis of the expressed enzymes, purified to homogeneity, revealed that the Ala445-hGDH2 variant displayed a basal specific activity that was substantially greater than that of the prevalent hGDH2. The specific basal activity of the variant was concentration-dependent (FIGS. 6&7), as also previously shown for hGDH2 but not for hGDH1. At enzyme concentrations of about 5 µg/ml, the basal specific activity of the variant approached that of hGDH1 (FIGS. 6 & 7), but in contrast to the latter this activity was resistant to suppression by GTP (Table 3).

TABLE 3

| | $IC_{50}$ (µM) | | | Hill Coefficient | | |
|---|---|---|---|---|---|---|
| | No ADP | 0.1 mM ADP | 1 mM ADP | No ADP | 0.1 mM ADP | 1 mM ADP |
| Ala445-hGDH2 | 29.06 ± 4.48 | 24.39 ± 2.62 | 257.8 ± 42.2 | 0.80 ± 0.05 | 1.01 ± 0.09 | 0.71 ± 0.04 |
| hGDH2 | 40.07 ± 4.46 | 12.22 ± 2.65 | 204.1 ± 36.4 | 0.72 ± 0.05 | 1.06 ± 0.16 | 0.82 ± 0.11 |
| hGDH1 | 0.31 ± 0.03 | 1.61 ± 0.02 | 18.51 ± 0.49 | 1.51 ± 0.07 | 2.13 ± 0.15 | 1.94 ± 0.07 |

In addition, the Ser445Ala change increased the thermal stability of the variant. On the other hand, the catalytic properties and the positive modulation by ADP and L-leucine of the variant were not substantially affected. See Tables 4 and 5 below.

TABLE 4

|  | $V_{max}$ μmol*min$^{-1}$*mg$^{-1}$ | $K_m$ Glutamate mM | α-Ketoglutarate Mm | Ammonia mM |
|---|---|---|---|---|
| Ala445-hGDH2 | 154.95 | 6.80 ± 1.90 | 2.67 ± 0.31 | 21.36 ± 3.56 |
| Ser445-hGDH2 | 159.12 | 10.69 ± 1.77 | 2.07 ± 0.29 | 17.05 ± 2.01 |
| hGDH1 | 161.89 | 12.44 ± 1.48 | 2.01 ± 0.18 | 13.39 ± 0.72 |

TABLE 5

|  | ADP SC$_{50}$ (μM) | L-leucine SC$_{50}$ (mM) |
|---|---|---|
| Ala445-hGDH2 | 58.2 ± 5.5 | 0.955 ± 0.045 |
| hGDH2 | 68.5 ± 2.3 | 1.015 ± 0.213 |
| hGDH1 | 22.4 ± 2.1 | 0.860 ± 0.139 |

Example 3

Estrogen Modification of Glutamate Oxidative Dehydrogenation Linked to State of Enzyme Activation As indicated above, the Ala445-hGDH2 variant enzyme displays a basal specific activity that was substantially greater than that of the wild-type hGDH2. This, at enzyme concentrations of about 5 μg/ml, approaches that of wild-type hGDH1, but in contrast to the wild-type hGDH1, the activity of the Ala445-hGDH2 variant is not regulated by GTP. These observations suggest that, while GDH activity in the brain is under normal conditions regulated, the activity of the variant may remain unregulated. As such, substitution of Ala for Ser445 by making the enzyme overactive it confers a gain-of-function property.

Mammalian GDH (hGDH1 in the human) is allosterically regulated with GTP and NADH acting as negative modulators and ADP as a positive modulator (Smith, 1979). In addition, several chemically diverse compounds such as L-leucine, palmityl-CoA, polyamines and steroid hormones are shown to influence GDH activity, but the mechanisms involved and the implications of this enzyme regulation in cell biology remain uncertain. On the other hand, the hGDH2 is resistant to inhibition by GTP although is responsive to ADP and L-leucine activation (Plaitakis et al 2000).

In search for inhibitors that are specific for hGDH2, taking into consideration evidence deriving from the study on Parkinson's disease that only G-hemizygous males showed the effect of the DNA variation on age at disease onset. It was surprising to see that G/T heterozygous females were not affected at a younger age; in fact, in all cohorts studied, the mean at PD development was somewhat higher in G/T heterozygous females than in other genotypic groups, although this difference was not significant. These results were the opposite of those expected on the basis of the gain-of-function hypothesis, as in other human disorders linked to gain-of-function DNA abnormalities, heterozygous show essentially the phenotype of hemizygotes (for X-linked genes) or of homozygotes (for autosomal genes). A clue to this paradox may lie on the female system and to explore this the effect of female hormones on wild-type hGDH1/2 and on the polymorphic enzyme was tested.

Figure 8:
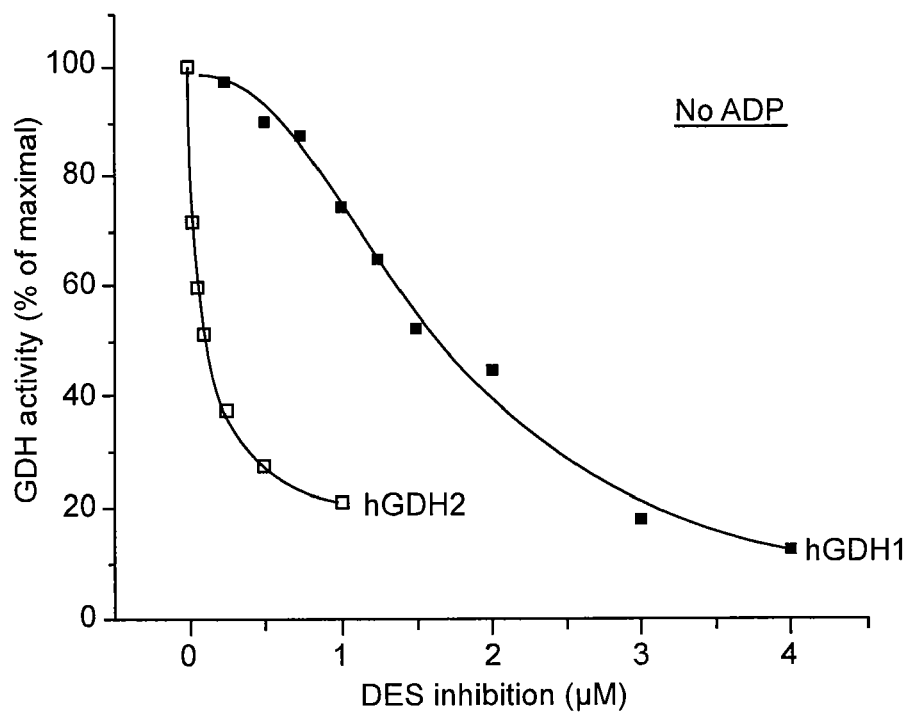
FIG. 8 is charted data of GDH activity versus DES inhibition in the absence of ADP.
Figure 9:
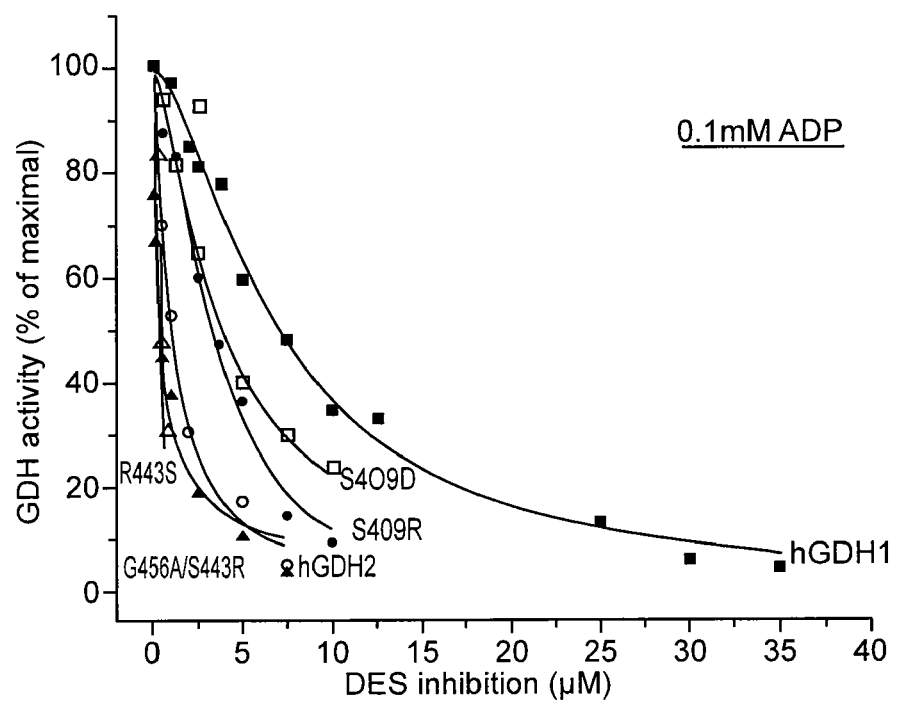
FIG. 9 is charted data of GDH activity versus DES inhibition in the presence of ADP.

For this, a study was performed on the interaction of estrogens with the hGDH2 variant as well as with the wild type-hGDH2 and hGDH1 obtained by expression of the corresponding cDNAs in Sf21 cells. Results revealed that the Ser445Ala variant was much more sensitive (P<0.001) to inhibition by estrogens (IC$_{50}$±S.E.=19±3 nmoles/lt DES) than the wild type housekeeping hGDH1 (IC$_{50}$±S.E.=1, 530±46 nmoles/lt DES) when tested under baseline conditions (in the absence of allosteric effectors) (Table 6; FIGS. 8 & 9).

TABLE 6

Inhibition of purified wild-type hGDH1 and hGDH2 and recombinant R443S by female steroidal hormones.

Table 6A. No ADP

|  | Basal Specific Activity (μmoles/min/mg) | IC$_{50}$ (μM) | | | |
|---|---|---|---|---|---|
|  |  | DES | 17 b-Estradiol | Oestriol | Progesterone |
| hGDH2 | 7.6 ± 0.1 | 0.09 ± 0.01 | 1.54 ± 0.23 | 11.34 ± 0.74 | 12.32 ± 2.63 |
| hGDH1 | 58.1 ± 4.1 | 1.67 ± 0.02 | 26.94 ± 1.07 | 144.77 ± 18.8 | 218.88 ± 7.99 |

Table 6B. 0.1 mM ADP

|  | Vmax (μmoles/min/mg) | Specific Activity at 0.1 mM ADP (μmoles/min/mg) | IC$_{50}$ (μM) | |
|---|---|---|---|---|
|  |  |  | DES | 17 b-Estradiol |
| hGDH2 | 159.2 ± 0.4 | 111.4 ± 1.4 | 1.05 ± 0.09 | 15.10 ± 1.21 |
| hGDH1 | 161.3 ± 0.5 | 148.4 ± 2.1 | 7.07 ± 0.40 | 69.22 ± 1.30 |
| Ser443-hGDH1 | 140.3 ± 0.3 | 14.0 ± 0.4 | 0.51 ± 0.05 | 2.22 ± 0.76 |

TABLE 6-continued

|  | Vmax (µmoles/ min/mg) | Specific Activity at 0.1 mM ADP (µmoles/ min/mg) | IC$_{50}$ (µM) Oestriol | IC$_{50}$ (µM) Progesterone |
|---|---|---|---|---|
| hGDH2 | 159.2 ± 0.4 | 111.4 ± 1.4 | 188.72 ± 17.90 | 392.21 ± 8.91 |
| hGDH1 | 161.3 ± 0.5 | 148.4 ± 2.1 | 315.53 ± 26.10 | 596.39 ± 50.1 |
| Ser443-hGDH1 | 140.3 ± 0.3 | 14.0 ± 0.4 | 2.43 ± 0.05 | 8.62 ± 1.23 |

Figure 10:
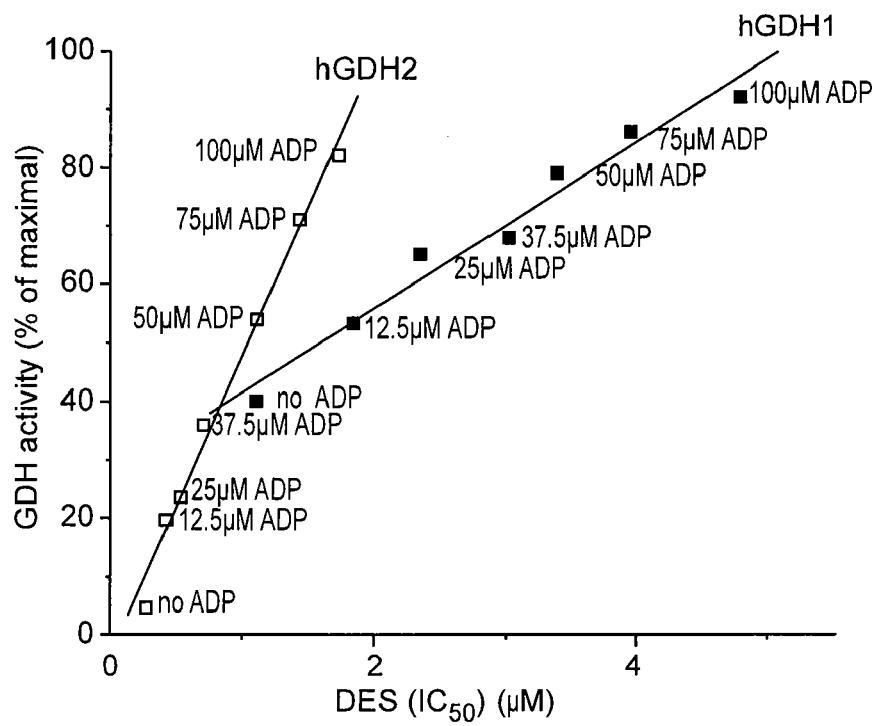
FIG. 10 is charted data of GDH activity versus DES.

The marked sensitivity of the Ser445Ala variant to estrogens was also evident when the enzyme was activated by 0.1 mM ADP or 1.0 mM ADP (FIG. 10). Also, under baseline conditions, hGDH2 was >15 fold more sensitive to diethylstilbestrol (DES) (IC$_{50}$=0.094 µM) than hGDH1 (IC$_{50}$=1.5 µM). Also, Estradiol, Oestriol and Progesterone inhibited hGDH2 more strongly than hGDH; however, these naturally occurring hormones were less potent inhibitors of human wild-type GDHs than the synthetic estrogen DES. Also, when activated by ADP (0.025-1.0 mM), hGDH2 remained more sensitive to estrogens than hGDH1 (FIG. 10).

Methods

Production and Purification of Recombinant hGDHs. The variant 1492G-GLUD2 cDNA, along with the GLUD1 and the GLUD2 cDNAs, were subcloned into pVL1392 and pVL1393 vectors and expressed in Sf21 cells using the baculovirus expression system. The produced recombinant hGDHs were purified from Sf21 cell extracts using a previously described method that involves Ammonium Sulfate fractionation, hydrophobic interaction and hydroxyapatite chromatography. The purification resulted in electrophoretically homogenous (>95% pure) hGDHs FIG. 5. All hGDH proteins studied were produced and analyzed in parallel.

Enzyme Assays. GDH activity was assayed spectrophotometrically at 25° C. in the direction of reductive amination of α-ketoglutarate. Initial rates (enzyme velocity at the interval during which the change in absorbance maintained linearity) were recorded. Kinetic analyses were performed to determine the Michaelis-Menten constant (K$_m$) for α-ketoglutarate, ammonia and glutamate. Regulation of the human recombinant GDHs by allosteric stimulators was studied by adding to the reaction ADP or L-leucine in various concentrations. Inhibition by GTP was studied by adding this compound in various concentrations to the reaction either in the absence of allosteric modulators or in the presence of 0.1 mM or 1.0 mM ADP. For the heat inactivation studies, samples containing about 50 µg/ml purified enzyme were incubated at 47.5° C. Aliquots were removed at specified time intervals and assayed immediately for enzyme activity.

Statistical Analysis. A t-test and chi-square test were performed to assess differences in the age and gender distribution, respectively, between patients and controls with a significance level of α=0.05. Pearson's x$^2$ and Fisher's exact tests (SPSS, v. 14.0) were used to evaluate differences in allele frequencies between cases and unaffected individuals. Independent samples t-test was used to examine the effect of GLUD-2 Ser445Ala genotypes on age at onset of PD. The analysis was performed in the combined, as well as in the stratified by gender group of patients. Analysis and plotting of the enzymatic data was performed using the Microcal Origin® program (Microcal Software Inc., Northampton, Mass.).

Discussion of Results

Wild-type hGDH2 and the Ser445Ala-hGDH2 variant hGDH2 are exquisitely sensitive to estrogens. Hence, steroid hormones are relatively selective inhibitors of the hGDH2 enzyme and its Ser445Ala variant. In light of these findings, estrogens in females may nullify the gain-of-function effects seen in male patients, by blocking the overactive variant enzyme from metabolizing increased amounts of glutamate (and in the process damaging the nigral cells).

The mechanisms by which the Ser445Ala-hGDH2 variant hastens the commencement of PD symptoms may provide a means for retarding the development of this disorder. To identify the structural basis for these effects, site-directed mutagenesis of the GLUD1 gene (encoding hGDH1) at amino acid residues that differ from those of the GLUD2 gene (encoding GDH2) revealed that substitution of Ser for Arg443 was solely responsible for the exquisite sensitivity of the nerve tissue human GDH to estrogens. The Arg443Ser change does not alter sensitivity to GTP, as the Ser443 hGDH1 polymorphism is as sensitive to this compound as is the wild-type hGDH1. Inactivation of the GTP sites may affect regulation of the protein by estrogens. For example, Arg443Ser/Gly456Ala double polymorphism (e.g., a double polymorphism of hGDH1 that, in addition to the Arg443Ser change, carries the Gly456Ala polymorphism) remained as sensitive to estrogens as the Arg443Ser single polymorphism (FIGS. 8&9).

Figure 11:
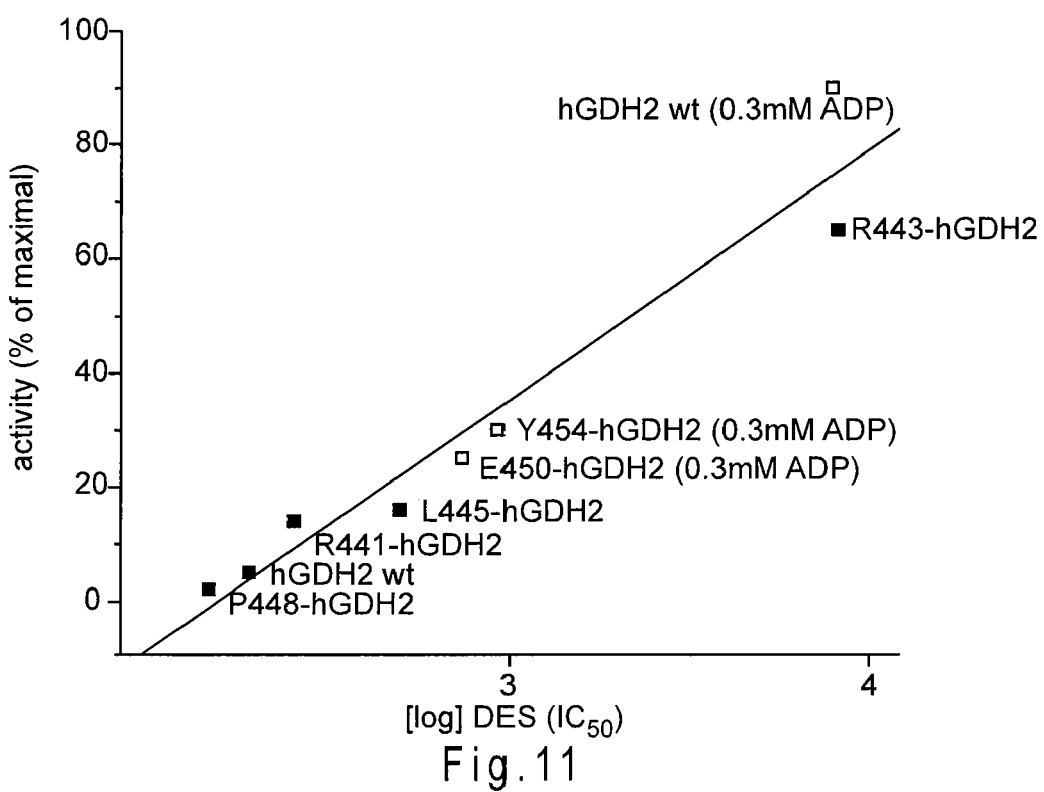
FIG. 11 is charted data of activity versus log DES.

The Arg443Ser single polymorphism displays a fraction of the basal activity of the wild-type. Modeling of the Arg443Ser change has shown that this substitution disrupts the H-bonds formed between the Arg-443 (located in a small α-helix of the descending stand of the antenna) of one GDH subunit and the Ser-409 (located in the ascending strand of the antenna) of an adjacent subunit leading to a close conformation. The validity of this model has been tested by creating an hGDH1 polymorphism in which Ser409 was replaced Arg, which also disrupts the above H-bonds diminishes basal by conferring a close enzyme conformation. Functional analyses of the Ser409Arg this polymorphism (expressed in Sf21 cells) revealed that it is markedly sensitive to estrogens (FIG. 11). Hence, these results are consistent with the concept that interaction of estrogens with GDH is potentiated by a closed enzyme conformation.

Experiment: Sensitivity of Human GDHs to Estrogens is Linked to State of Enzyme Activation In light of the above results, whether the steroid effect is linked to the state of activation of the enzyme was analyzed. For this two different approaches were used: the first involved the study of estrogen interaction with wild type hGDH1 or wild-type hGDH2 at different states of activation induced by ADP, a positive enzyme modulator capable of maintaining an open conformation, and the second approach involved the study of polymorphisms in hGDH1 and hGDH2 that affect basal activity.

Steroid Inhibition in the Presence of ADP

Study of the inhibitory curves of the two human isoproteins, obtained at specific ADP concentrations, revealed that modification of either hGDH1 or hGDH2 by estrogens correlated inversely (R=0.9845 for hGDH1, R=0.9935 for hGDH2) with their state of activation (catalytic activity at 0 estrogen concentration). However, the obtained regression line for hGDH2 was significantly steeper for hGDH2 than for hGDH1 indicating that the estrogen effect is linked stronger to the state of activation of the nerve tissue (hGDH2) than of the housekeeping, hGDH1.

Study of hGDH1 and hGDH2 Mutants Reveals that Sensitivity to Estrogens Correlates Inversely with their Specific Basal Activity Since wild-type hGDH2 shows in the absence of modulators only a fraction of the catalytic activity of hGDH1, it was sought to determine whether estrogen sensitivity is a general property linked to low basal activity and whether attenuation of this sensitivity can occur independently of ADP activation. For this, the GLUD1 and GLUD2 genes were mutated at specific sites and estrogen interaction with the polymorphic proteins (expressed in Sf21 cells) was studied and reveal altered basal activities.

Mutagenesis of the GLUD2 gene produced five hGDH2 mutants, the basal activity of which was different than that of the wild-type hGDH2. Of these, the Lys450Glu and His454Tyr mutants (with an amino acid substitution in the pivot helix) showed a basal activity that was lower than that of wild-type hGDH2, whereas the Gln441Arg and Ser445Leu mutants (with an amino acid replacement in the antenna) displayed an enhanced basal activity. On the other hand, the Ser448Pro polymorphism, located in the junction of the antenna with the pivot helix, was associated with reduced basal activity.

Figure 3:
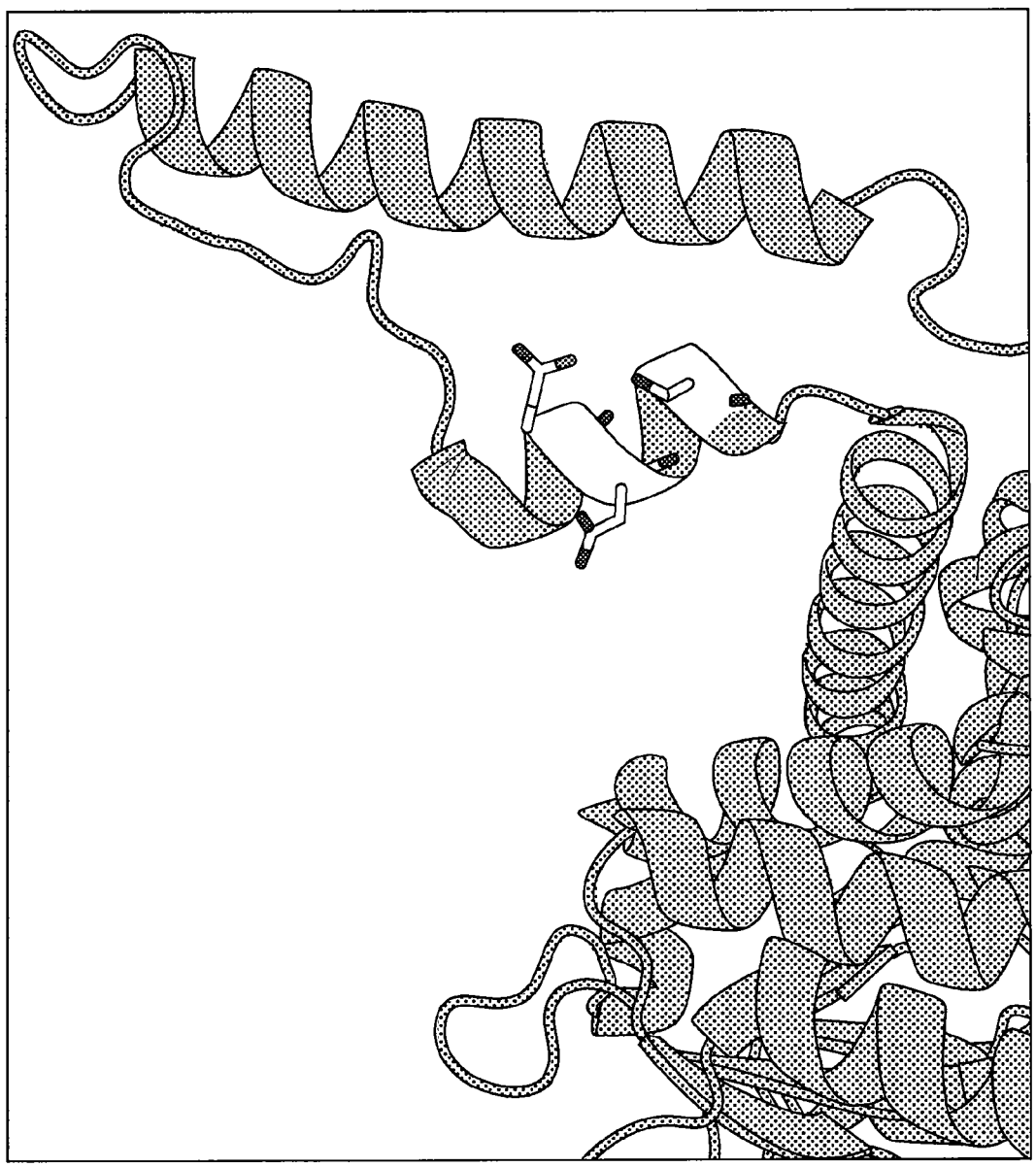
FIG. 3 is an exemplary diagram of the antenna region of one of the six hGDH subunits.
Figure 4:
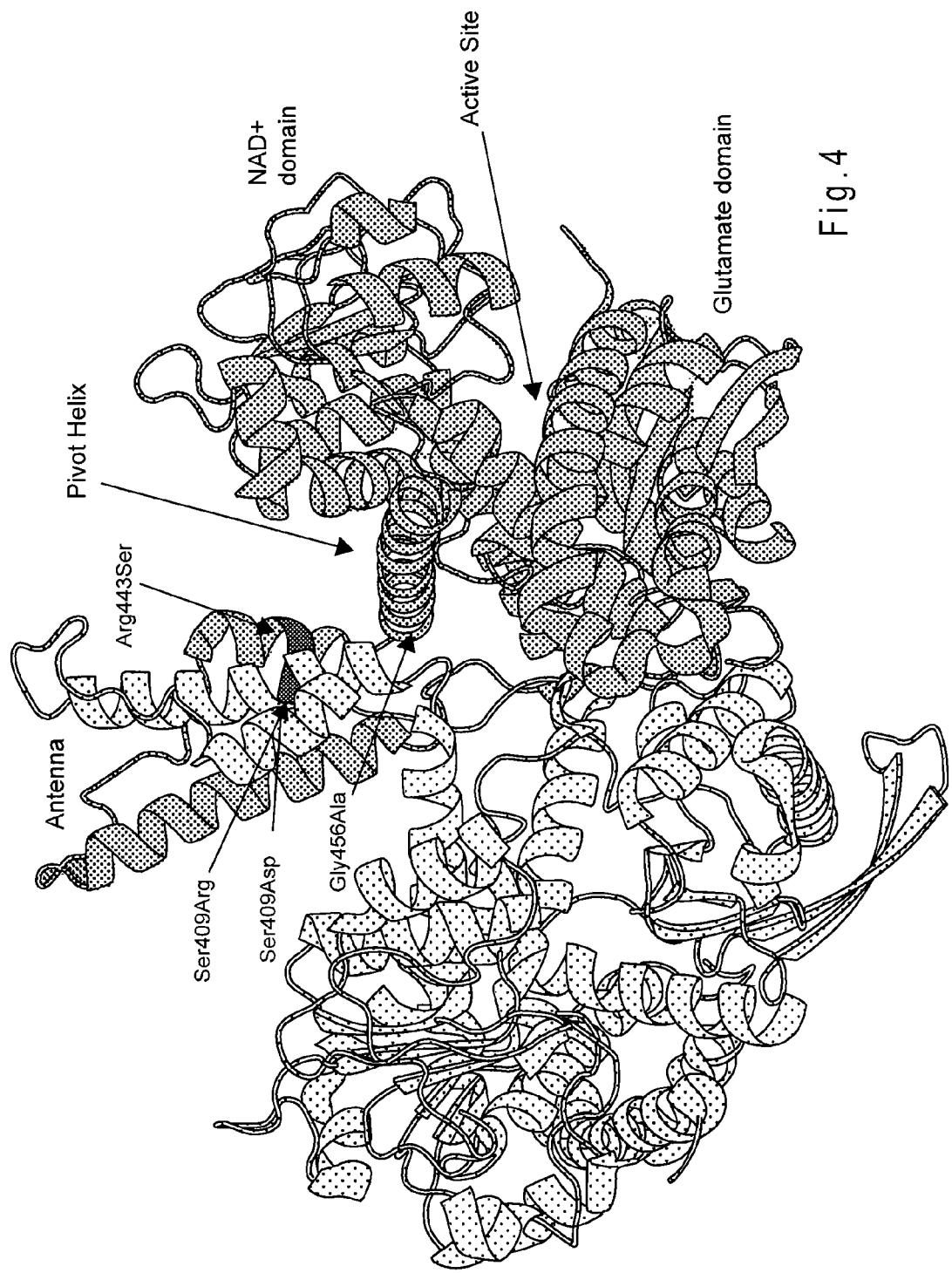
FIG. 4 is an exemplary diagram showing the location of the introduced mutations in hGDH1.

FIGS. 3 & 4 Shows the location of the introduced mutations in hGDH1 (FIG. 4) and in hGDH2 (FIG. 5) in a diagram of the apo form of human GDH1 (PDB entry 1-LIF) (Smith et al., 2002). For simplicity, only two of six subunits that compose the GDH hexamer are shown (green or blue), including their NAD+-binding domain, the glutamate-binding domain, the active site, the pivot helix and the antenna. Residues that differ between hGDH1 and hGDH2 are shown in yellow. Mutations studied in hGDH1 (Arg443Ser, 409Arg/Asp) or in hGDH2 (Lys450Glu, Hist454Tyr, Ser448Pro) that decrease basal activity are shown in red. The reverse mutation in hGDH2 (Ser443Arg) that markedly increases basal activity is shown in purple.

Figure 12:
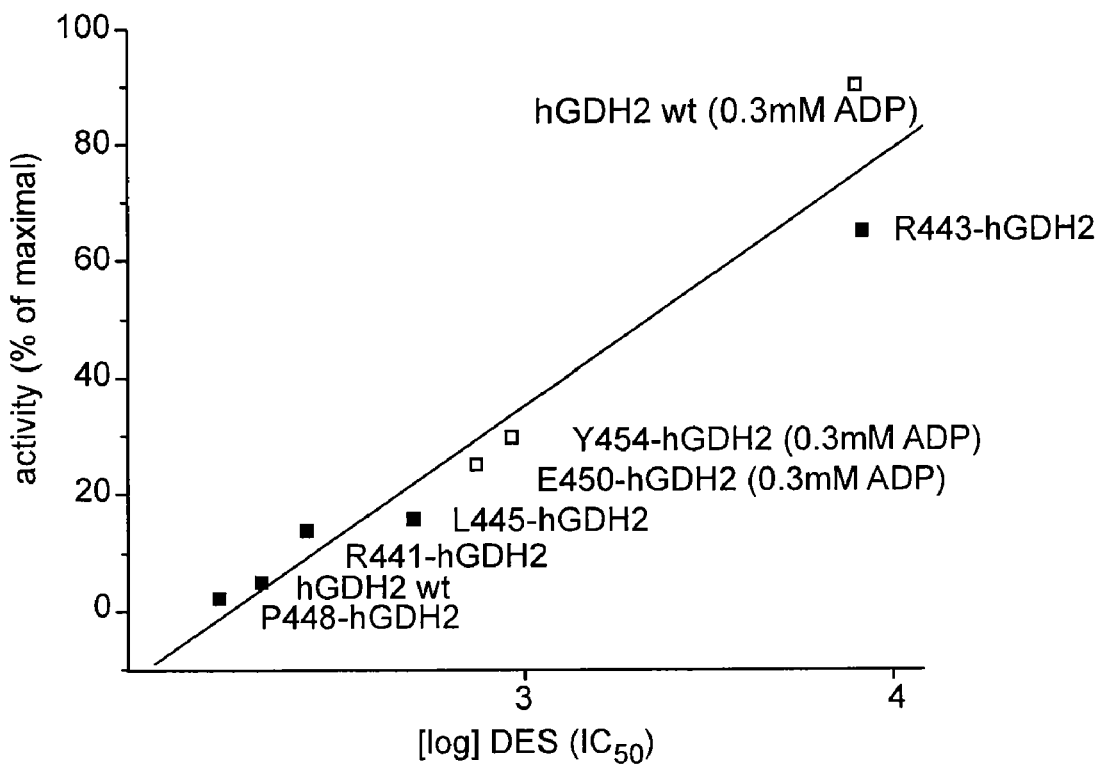
FIG. 12 is charted data of activity versus log DES.

Functional analyses showed that the sensitivity of these hGDH2 mutants correlated inversely (R=0.97752) with their basal activity levels. Also, mutagenesis of GLUD1 gene produced four hGDH1 mutants with altered basal activities. Regression analyses of these enzymes revealed a similar inverse correlation between the sensitivity of these enzymes to estrogens (R=0.9808) and their basal activity levels (FIG. 12).

Similar results were obtained when all these mutant and wild-type human GDHs were activated by ADP (R=0.97395). As such, these results confirm that steroid sensitivity relates inversely to the state of enzyme activation.

Production of Recombinant Wild-Type and Mutant hGDH1 and hGDH2 and Their Modification by Estrogens in Crude Extracts—Expression of the wild-type GLUD1 and GLUD2 genes in Sf21 cells produced catalytically active human enzymes, as previously described (Kanavouras et al., 2007). Initial studies using crude homogenates revealed that the steroid hormones tested, acting in a concentration-dependent manner, inhibited the wild-type hGDH2 more potently than the wild-type hGDH1. To determine the amino acid residue(s) responsible for this sensitivity of hGDH2, functional analyses of single amino acid mutants was performed, and mutants obtained by mutagenesis of the GLUD1 gene at residues that differ from the GLUD2 gene. These studies revealed that the Arg443Ser hGDH1 mutant (but not Glu34Lys, Arg39Gln, Asp142Glu, Ile166Val, Ser174Asn, Gly247Arg, Ala321Val or Gly456Ala) was exceptionally sensitive to estrogens. Following these results, the wild-type hGDH1 and hGDH2 and the Arg443Ser mutant were further studied after they were purified to homogeneity as described below.

Purification of Recombinant Wild-Type and Mutant hGDHs—Using extracts of Sf21 cells expressing wild-type hGDH1 or hGDH2, or the Arg443Ser hGDH1 mutant were purified to homogeneity using a previously described procedure (Kanavouras et al., 2007). Also, as described below, the Arg443Ser/Gly456Ala double mutant and the Ser409Arg/Asp single mutants of hGDH1 and the Ser445Ala mutant of hGDH2 were studied after they were purified to homogeneity using extracts of Sf21 cells expressing these proteins. Enzyme recoveries and degree of purification of the final products were similar to those of the wild-type hGDH1 and hGDH2. Also, the expressed wild-type hGDH1 and hGDH2 displayed the expected kinetic and regulatory properties, as previously described (Kanavouras et al., 2007).

Modification of Purified Wild-Type hGDH1 and hGDH2 by Estrogens—Functional analyses of the purified wild-type human enzymes confirmed that estrogens interacted more potently with the wild-type hGDH2 than with the wild-type hGDH1. Thus, under baseline conditions hGDH2 was ~18-fold more sensitive to diethylstilbestrol (DES) ($IC_{50}$=0.094 μM) than hGDH1 ($IC_{50}$=1.7 μM). Similarly, 17 beta-estradiol showed a ~18-fold higher affinity for hGDH2 ($IC_{50}$=1.5 μM) than for hGDH1 ($IC_{50}$=26.9 μM). Also, oestriol and progesterone inhibited hGDH2 more strongly than hGDH1, but at higher concentrations than those required for DES or 17 beta-estradiol (Table 6A). Also, the differential effects of these hormones on the wild-type hGDH1 and hGDH2 were less prominent than those obtained with the use of DES and 17 beta-estradiol (Table 6A)

Figure 7:
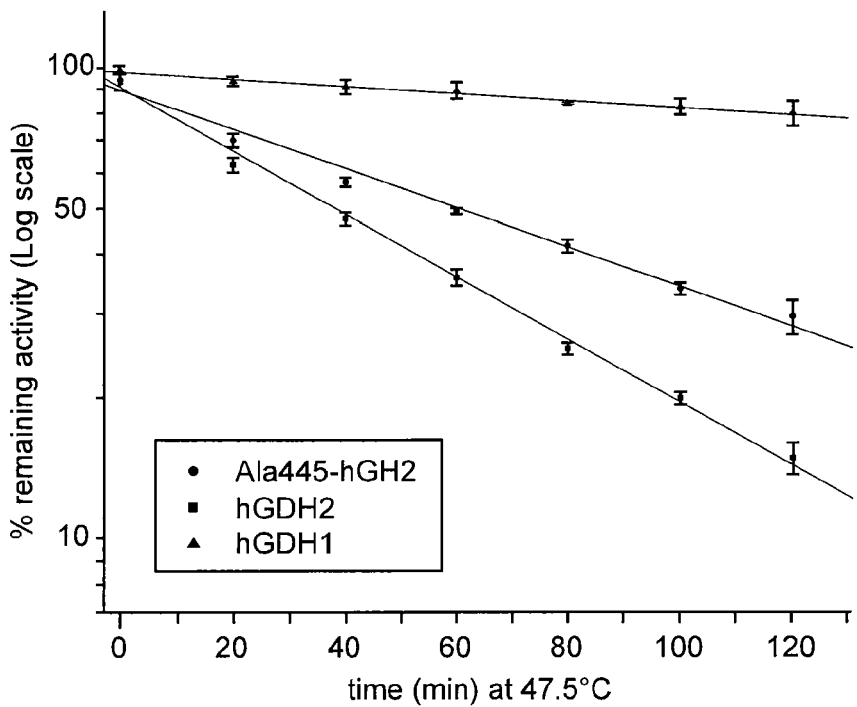
FIG. 7 is charted data representing percent remaining activity versus time.

When the two human wild-type enzymes were activated by ADP, hGDH2 again proved to be more sensitive to estrogens than hGDH1 (FIG. 7; Table 6B). Study of the inhibitory curves of the two human isoproteins, obtained at specific ADP concentrations, revealed that modification of either hGDH1 or hGDH2 by estrogens correlated inversely with the level of catalytic activity measured prior to the addition of the female hormones (R=0.9845 for hGDH1, R=0.9935 for hGDH2). However, the obtained regression line for hGDH2 was significantly steeper than that for hGDH1, indicating that the estrogen effect is linked stronger to the state of activation of the nerve tissue than that of the housekeeping GDH.

Figure 13:
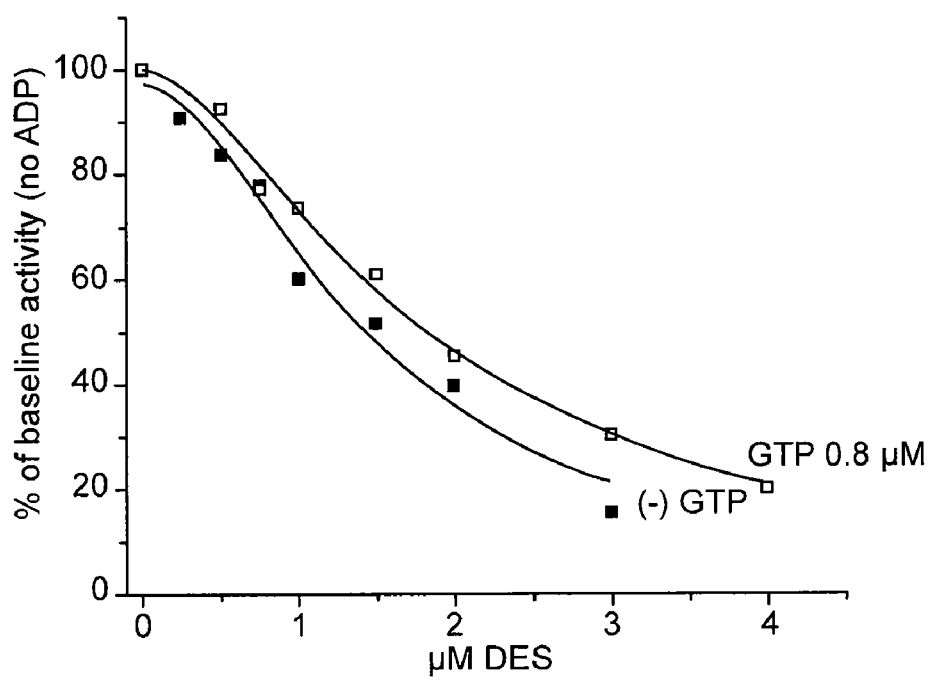
FIG. 13 is charted data of percent baseline activity versus DES.

As hGDH1 activity is inhibited potently by GTP, investigation focused on whether the presence of inhibitory concentrations of GTP alters the enzyme's sensitivity to estrogens. Results revealed that, when assays were performed in the absence of allosteric activators, inhibitory concentrations of GTP had no effect on the modulation of hGDH1 activity by estrogens (FIG. 13).

Figure 14:
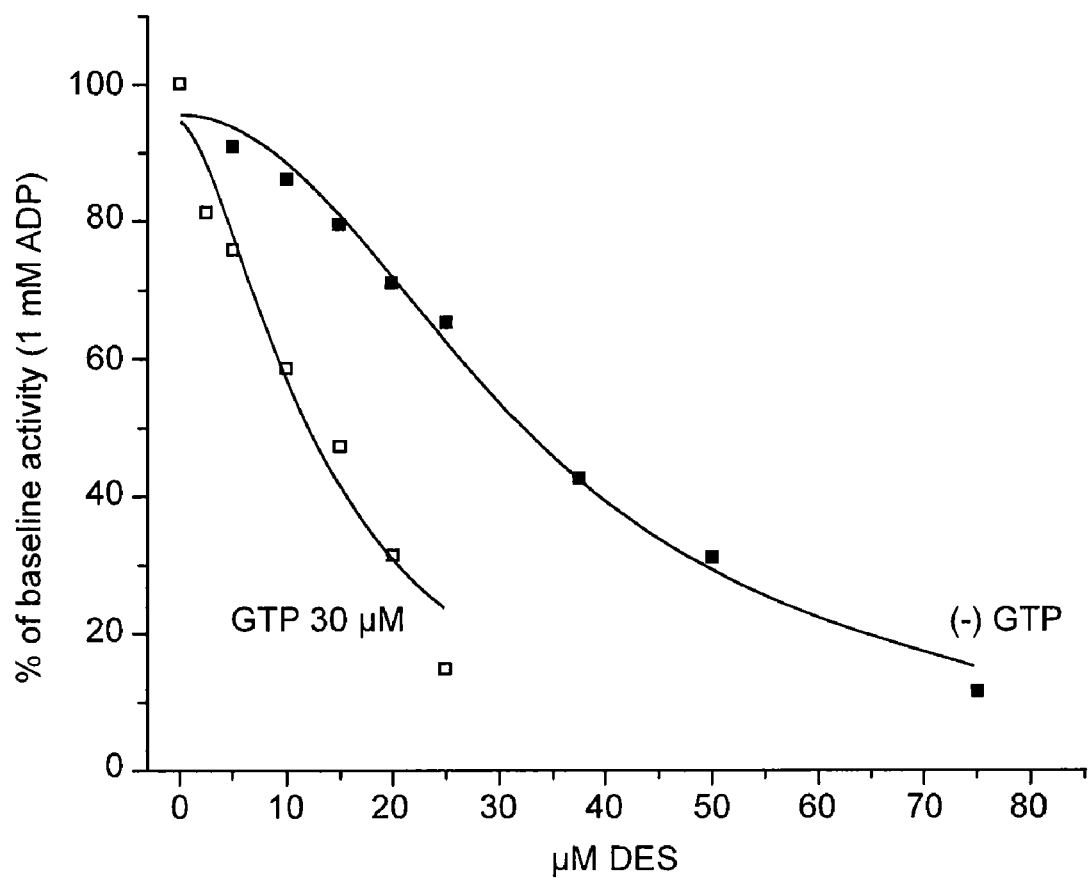
FIG. 14 is charted data of percent baseline activity versus DES.

However, when hGDH1 was activated by ADP, the presence of inhibitory concentrations of GTP potentiated the interaction of estrogens with this human isoenzyme (FIG. 14).

Figure 15:
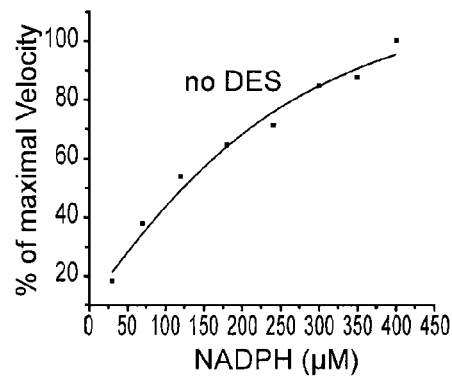
FIG. 15 is charted data of various kinetic analyses of NADPH binding in the presence of DES concentrations.
Figure 15:
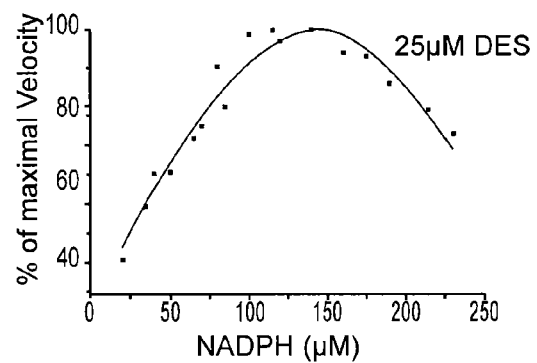
Figure 15:
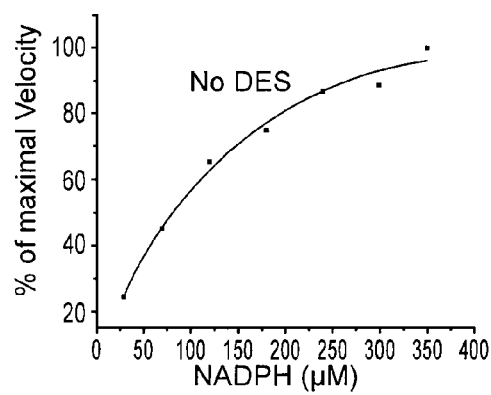
Figure 15:
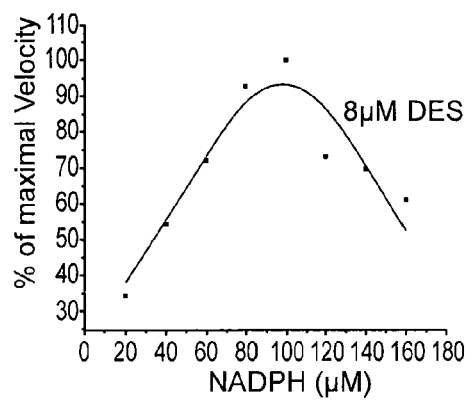

Modification of Kinetic Properties of Wild-Type hGDH1 and hGDH2 by Estrogens—Kinetic analyses performed by varying the levels of the enzyme's substrates in the presence of inhibitory concentrations of DES revealed that the Km for α-ketoglutarate, $NH_3$ or glutamate was not altered by the inhibitor. However, kinetic analyses of NADPH binding in the presence of DES concentrations sufficient to decrease the activity of hGDH1 or hGDH2 by 50% ($IC_{50}$ for each of the wild-type enzymes) revealed that the estrogen provoked enzyme inhibition by excess co-factor (NADPH>100 μM). In contrast, in the absence of DES, no enzyme inhibition was observed by excess co-factor (studied up to 400 μM of NADPH) of either wild-type hGDH1 or hGDH2 (FIG. 15).

Figure 16:
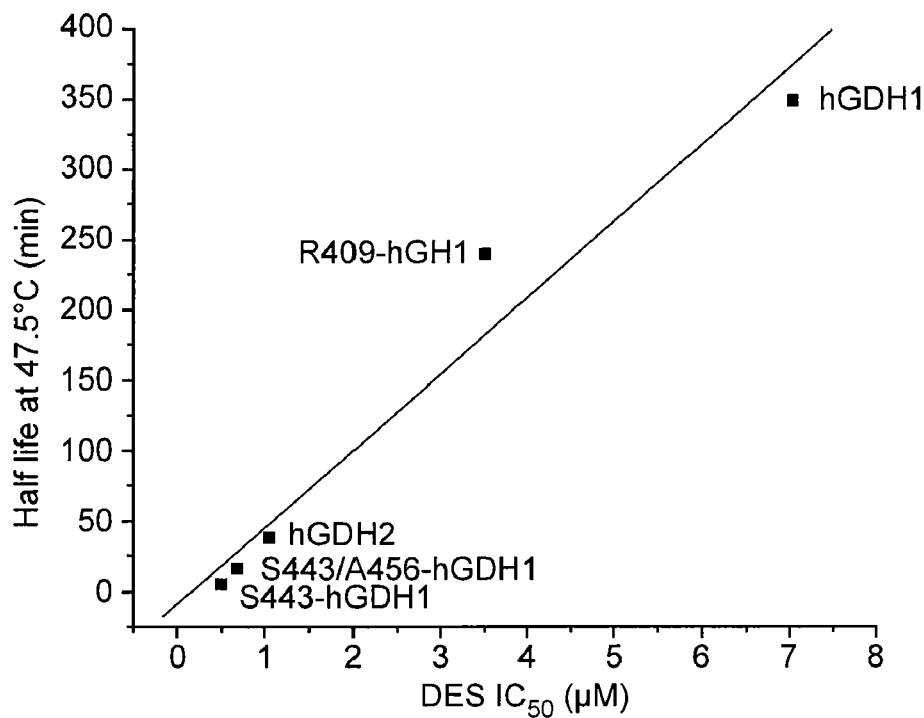
FIG. 16 is half life at 47.5 degrees C. versus DES.

Substitution of Ser for Arg443 is Responsible for the Sensitivity of hGDH2 to Estrogens—Functional analyses of the purified Arg443Ser hGDH1 mutant revealed that this mutant was 14-32 folds more sensitive to estrogens than the wild-type hGDH1 (Table 2B; FIG. 9). Since substitution of Ser for Arg443Ser in hGDH1 diminishes basal activity without altering GTP regulation (Zaganas et al., 2002), the present results suggest that the exceptional sensitivity to estrogens displayed by the Arg443Ser mutant relates to the closed enzyme conformation induced by this polymorphism irrespectively of the presence of functional GTP sites. This was further tested by studying a double mutant of hGDH1 that, in addition to the Arg443Ser change, carries the Gly456Ala polymorphism that confers resistance to GTP. Results showed that the Arg443Ser/Gly456Ala double mutant is as sensitive to estrogens as the Arg443Ser single mutant. That substitution of Ser for Arg443 is responsible for the sensitivity of the wild-type hGDH2 to estrogens was confirmed by reverse mutagenesis experiments in which the Ser443 of hGDH2 was replaced by Arg. Thus, functional analyses of the Arg443-hGDH2 mutant revealed that the introduced amino acid change completely abrogated the sensitivity of the mutant to estrogens while increasing its diminished basal activity to higher than that of the wild-type hGDH1 (FIG. 16).

As such, these results further confirm that replacement of Ser for Arg443 was the key evolutionary change that provided hGDH2 with a novel molecular mechanism for regulating its activity.

Figure 5:
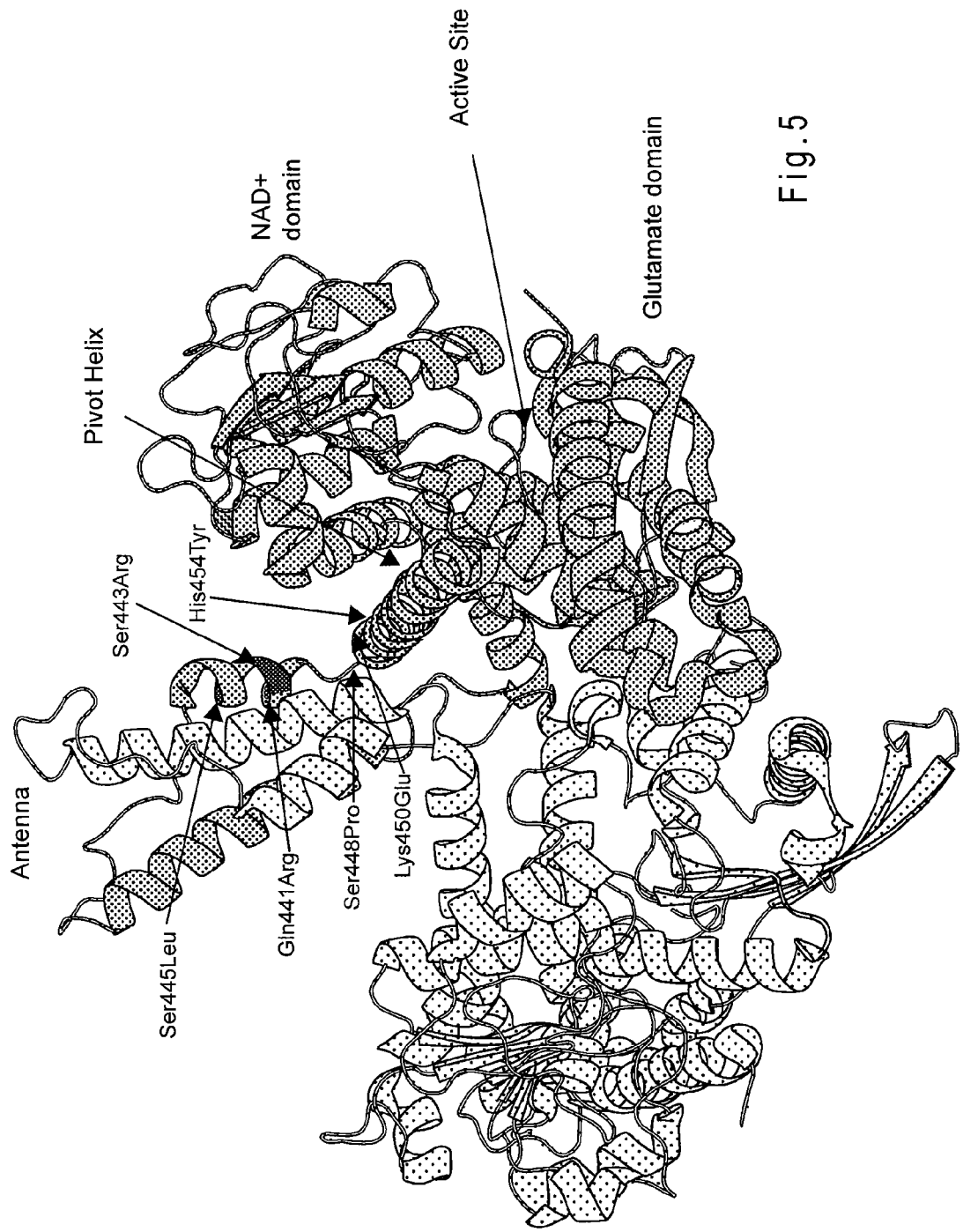
FIG. 5 is an exemplary diagram showing the location of the introduced mutations in hGDH2.
Figure 17:
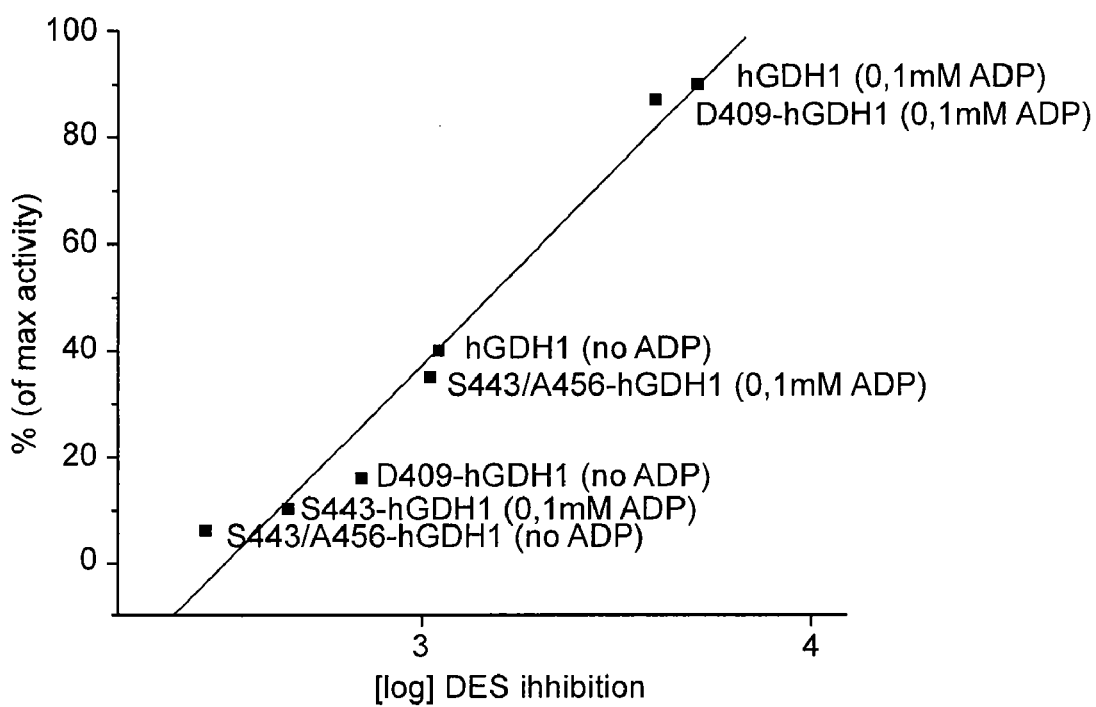
FIG. 17 is percent of max activity versus DES inhibition.

Study of hGDH1 and hGDH2 Mutants Reveals that Sensitivity to Estrogens Correlates Inversely with Their Specific Basal Activity—Since the Arg443Ser mutant displays a fraction of the basal activity of the wild-type hGDH1, whether other single amino acid substitutions in hGDH1 that affect basal activity alter sensitivity to estrogen hormones was tested. To this end hGDH1 mutants obtained by substitution of Arg or Asp for Ser409 were studied. These, similar to the Arg443Ser hGDH1 polymorphism, may decrease basal activity by disrupting side chain bonds in the antenna region between Arg443 of one subunit and Ser409 of the adjacent subunit (Mastorodemos et al., unpublished data). FIG. 4. Functional analyses of the purified Ser409Arg and Ser409Asp hGDH1 mutants indeed revealed that are markedly sensitive to estrogens (FIG. 9), thus supporting the possibility that estrogen interaction with GDH is potentiated by a close enzyme conformation. This possibility was further tested by studying several hGDH2 mutants obtained by mutagenesis of residues in the regulatory domain of GLUD2 that affect basal activity (Kanavouras et al., 2009). Of these, two pivot helix mutants obtained by substitution of Glu for Lys450 and Tyr for His454Tyr as shown in FIG. 5, show a basal activity that is substantially lower than that of the wild-type hGDH2 (Kanavouras et al., 2009). In contrast, two mutants of hGDH2 located in the antenna region (Gln441Arg and Ser445Leu) display an enhanced basal activity, whereas a third mutant that is located in the junction of the antenna with the pivot helix (Ser448Pro) decreased basal activity. FIG. 5. Results revealed that all three polymorphisms that depressed basal activity further (Lys 450Glu, Hist454Tyr and Ser448Pro) made the enzyme more sensitive to estrogens than the wild-type hGDH2, whereas the two polymorphisms that enhanced basal activity (Gln441Arg and Ser445Leu) attenuated estrogen inhibition. Regression analyses revealed that inhibition of mutant and wild-type hGDH2 by DES correlated inversely with their catalytic activity levels (R=0.9660) (FIG. 16). This was also true for the wild hGDH1 and its mutants (R=0.9864) (FIG. 17).

In addition, there was a significant correlation between enzyme basal activity and relative resistance to thermal inactivation (r=0.97719)

Discussion & Applications

The regulatory domain of GDH contains an antenna-like structure thought to mediate interaction between the enzyme's subunits. Residue 445 is on a small a-helix in the descending strand of the antenna that undergoes major conformational changes upon catalysis. Polymorphisms in residues (including Ser445) located in this helix of hGDH1 which attenuate GTP inhibition, are held responsible for some of the cases of the hyperinsulinism-hyperammonemia (HI/HA) syndrome. As GTP binds only to the closed conformation, these polymorphisms may abrogate GTP inhibition by stabilizing the helix and thereby favouring the open configuration. In hGDH2, replacement of Ser445 by Ala did not affect GTP sensitivity, because the evolutionary Gly456Ala substitution had already made the brain isoenzyme insensitive to GTP.

Substitution of Ala for Ser445 is predicted by secondary structure prediction programs to stabilize the small α-helix of the antenna. A similar stabilizing effect has also been suggested for the Ser445Leu change in hGDH1. Both Ala and Leu are considered to be better α-helix formers than Ser. Stabilization of the alpha helix would favour an open mouth conformation thereby counteracting the capacity of the evolutionary Arg443Ser change of hGDH2 to minimize basal activity.

In brain, glutamate is distributed in multiple pools, the maintenance of which requires the operation of transport systems and metabolizing enzymes, including GDH. Whereas glutamate oxidation in brain proceeds mainly via transamination, the GDH-catalyzed reaction assumes importance under conditions of intense excitatory transmission. Under pathological conditions (e.g. rotenone toxicity model for PD) glutamate oxidizing brain mitochondria generate increased amounts of ROS. Hence, it is likely that augmentation of glutamate oxidation by the Ala445-hGDH2 could accelerate an ongoing degenerative process in PD by altering the compartmented metabolism of glutamate in brain and/or by increasing ROS production. Since the Ser445Ala-hGDH2 polymorphism, which renders the enzyme hyperactive hastens the commencement of PD symptoms, decreasing the function of this enzyme could provide a means for retarding the development or progression of this disorder.

Illustrated is a method of removing or reducing an abnormality in the glutamate metabolism pathway, wherein the pathway contains a polymorphism of the GDH enzyme, e.g., the GLUD2 polymorphism described above, and a polymorphic GDH enzyme binding partner. Also illustrated are compositions and methods for the treatment of disorders which involve modulating the activity and/or level of individual components, and relates to methods for the identification of agents for such treatments. Additionally, illustrated are methods and compositions for prognostic evaluation of such disorders.

Described herein are compositions and methods for treating, preventing, retarding the onset of, and slowing the progression of disorders in which the hGDH2 enzyme has a Ser445Ala polymorphism. Additionally, described herein are composition and methods for prognostic evaluation of disorders in which the hGDH2 enzyme has a Ser445Ala polymorphism, for example, neurodegenerative disorders such as PD. Alterations in the function of hGDH2 may also affect adversely others organs where the GLUD2 gene is expressed, such as the testis, contributing, for example, to altered function of the sperm cells, hypogonadism, or male infertility. Alterations of the function of hGDH2 may also contribute to altered activity in melanoma cell lines. The novel discovery of estrogen's affinity for hGDH2 over hGDH1 may be used for the development of treatments for these disorders, including the treatment of melanomas.

In addition, since the present data suggests that an overactive GDH2 may deplete brain tissue of its glutamate content, a reduction in this amino acid pool may impair many functions of the brain including the so called malate aspartate shuttle. The operation of which requires aspartate supply from glutamate deamination. Another therapeutic route could be based on means to increase the CNS glutamate or aspartate content. Other pathways may be used.

Additionally or alternatively, illustrated are methods of slowing and/or retarding neurodegeneration by controlling (inhibiting) of GDH activity in individuals who have, for example but not limited to, spinal cord injury, stroke, traumatic brain injury and/or neurogenerative diseases of the central nervous system (CNS) such as Multiple sclerosis, Alzheimer's disease, Amyotrophic lateral sclerosis (ALS), Parkinson's disease, and Huntington's disease. These methods may include delivery to the patient of inhibitors that are specific for the mutant hGDH2 site, including but not limited to antigen specific antibodies and estrogens.

For example, reported herein is that estrogen hormones are relatively selective inhibitors of the GLUD2 gene-encoded hGDH2, an isoform of human glutamate dehydrogenase that arose through duplication in the ape ancestor and that is expressed in neural tissues, testicular tissues, and melanoma cells lines. To identify the structural basis for these effects, site-directed mutagenesis ewas performed of the GLUD1 gene at amino acid residues that differ from those of the GLUD2 gene and revealed that the evolutionary substitution of Ser for Arg443, that confers low basal activity to hGHD2, was solely responsible for the sensitivity of the nerve tissue human GDH to estrogens.

As modeling of the Arg443Ser change has suggested that the introduction of Ser-443 disrupts side chain bonds between adjacent subunits in the antenna region leading to a close conformation, we tested whether other single amino acid substitutions in hGDH1 or in hGDH2, that affect basal activity levels, alter sensitivity to estrogen hormones. In addition, the interaction of estrogens with the wild-type hGDH1/hGDH2 was studied and interaction with the above mutants in the presence of various concentrations of ADP, a positive modulator that activates the enzyme by helping the catalytic cleft to open (Smith and Stanley, 2008).

Results of these investigations revealed that the inhibitory potency of estrogens ($IC_{50}$) correlated inversely with the baseline activity levels (measured in the absence of ADP) of the hGDH1 and hGDH2 mutants studied. The same inverse correlation (R=0.9864) was found between the inhibitory potency of estrogens ($IC_{50}$) and the state of enzyme activation (catalytic activity over the baseline) induced by ADP. Also, since the thermo-stability of wild-type and mutant hGDHs relates to basal activity levels (Zaganas et al., 2009), performed additional analyses were performed which revealed that interaction of estrogens with the wild-type and mutant human GDHs correlated significantly (r=0.97719) with their sensitivity to thermal inactivation.

The data suggest that the molecular mechanisms by which estrogens exert their inhibitory effects on human GDHs are distinct from those of GTP, a negative allosteric modulator that promotes the close conformation, increasing the binding affinity for the product (Smith and Stanley, 2008). Thus, while wild-type hGDH2 is relatively resistant to GTP, this isoenzyme proved to be sensitive to estrogens. Conversely, the wild-type hGDH1, which is sensitive to GTP, proved relatively resistant to modulation by estrogens. Hence, while GTP acts as a specific inhibitor for hGDH1, estrogens influence the activity of the hGDH2 isoenzyme relatively selectively.

Consistent with this concept are the findings that the Gly456Ala single hGDH1 mutant that is resistant to GTP, as well as the Arg443Ser/Gly456Ala double hGDH1 mutant that displays both low basal activity and resistance to GTP inhibition (Mastorodemos et al., 2005), were found to be sensitive to estrogens. In addition, partial inhibition of hGDH1 by GTP did not sensitize the enzyme to estrogen modulation under baseline conditions. Only when the GTP effect was partially counteracted by ADP did the presence of GTP modify estrogen modulation. As such, it can be concluded that oestrogen inhibition of GDH does not require the GTP sites to be functional.

As described above, analyses of mutated human GDHs revealed that estrogens have potent effects on mutant enzymes that acquired low basal activity as a result of single amino acid substitutions. These polymorphisms, though acting from different parts of the GDH molecule have in common the ability to decrease basal activity probably by favouring a "close state" (Kanavouras et al., 2009). Hence, the present data, taken together with results of previous investigations, suggest that the major functional properties of hGDH2 (that distinguish it from hGDH1) can be attributed to two amino acid substitutions acquired during its molecular evolution. The first was substitution of Ala for Glyc456, which dissociated the enzyme's function from GTP control, and the second replacement of Arg443 by Ser, which lowered basal activity and at the same time conferred sensitivity to estrogens.

While inhibition of mammalian GDH by estrogens was one of the earliest observations on the direct effects of these hormones on metabolic enzymes (Yielding and Tompkins, 1960), modification of FoF1 ATPase, an enzyme central in ATP production or hydrolysis, by estrogens has received more attention lately (Zheng and Ramirez, 1999, 2000). It is presently unclear, however, whether these direct effects described previously are biologically relevant, as the concentrations required for inhibition of bovine liver GDH (hGDH1 in the human) or of FoF1 ATPase (26 µM-145 µM) are above the physiological levels of these hormones. Hence, the present findings, showing that hGDH2 is much more sensitive to estrogens than hGDH1 or FoF1 ATPase, suggest that these hormones (at their physiological concentrations) may target, among the metabolic enzymes, hGDH2 preferentially.

The present study showed that the affinity of estrogens for hGDH1 or for hGDH2 correlates inversely with the state of activation of these enzymes. The sensitivity of hGDH2 to these hormones can be explained (at least in part) by the propensity of this enzyme to assume under baseline conditions a closed conformation. Since ADP acting as a positive modulator of the human enzyme can antagonize estrogen inhibition, regulation of hGDH2 may be achieved by the opposing actions of estrogens and ADP, akin to the regulation of hGDH1 by the antagonistic effects of GTP and ADP on this isoenzyme. It has been argued (Plaitakis et al., 2000) that hGDH2 has adapted to the unique environment that prevails in the nerve tissue in which GTP levels are higher than those found in other tissues. Moreover, resistance to GTP inhibition may allow hGDH2 to function in nerve terminals even when the TCA cycle generates GTP levels sufficient to inhibit hGDH1. The other molecular adaption detected here, namely selective inhibition of hGDH2 by estrogens, may permit these hormones along with ADP to dynamically modulate nerve tissue glutamate metabolism under changing metabolic and energy demands.

Previous studies have shown that estrogens in brain modulate aspects of glutamate function, exerting protective effects against glutamate excitotoxicity and oxidative stress (Amantea et al., 2005). There is also evidence that estrogens modify glutamatergic transmission by increasing the expression of glutamine synthetase, a glial enzyme that synthesizes glutamine to be used as precursor of neurotransmitter glutamate. As inhibition of glutamate flux through GDH may permit a larger fraction of this amino acid to enter the glutamine synthetase pathway, with the produced glutamine being transferred to neurons to be used for renewing their glutamate transmitter pools (Waniefski and Martin, 1986; Sonnewald et al., 1997), regulation of hGDH2 by estrogens may represent another mechanism by which these hormones could enhance the continuing production of neuronal glutamate.

While normal control of GDH velocity is of importance for cell functions, abnormal enzyme regulation may lead to disease processes in the human. Thus, children affected by the hyperinsulinism/hyperammonia syndrome (HI/HA) are shown to harbor in their GLUD1 gene gain-of-function polymorphisms (Stanley et al., 1998, 2000). These polymorphisms, by attenuating GTP inhibition, result in a hyperactive hGDH1 that causes enhanced insulin secretion through increased ATP levels. In addition, enhanced glutamate oxidation results in decreased synthesis of N-acetylglutamate, a compound needed in the operation of the urea cycle.

Regarding the possible role of hGDH2 malfunction in neurologic disorders, studies in patients with Parkinson's disease (PD) have shown that a non-synonymous change (T1492G) within the coding region of the GLUD2 gene (resulting in the substitution of Ala for Ser445 in the regulatory domain of hGDH2) affected age at disease onset. Thus, genotyping of Parkinson's disease patients from two populations of diverse genetic backgrounds revealed that hemizygous subjects for the Ser445Ala hGDH2 variant developed PD 8-13 years earlier than patients with other genotypes, including female subjects heterozygous for this polymorphism (Plaitakis et al., unpublished data). The Ser445Ala-hGDH2 enzyme, obtained in recombinant form by expressing the variant GLUD2 cDNA in Sf21 cells using the baculovirus expression system, displayed gain-of-function properties but remained sensitive to estrogens. Lack of effect of the DNA polymorphism in female heterozygotes has been attributed to the inhibitory effects of female hormones on the hGDH2 variant (Plaitakis et al., unpublished results). Also, independent studies (Morissette et al., 2008) have provided evidence that female hormones protect from Parkinson's disease. Whether these positive effects of estrogens in nigral cell degeneration are linked to attenuation of enhanced hydroxyl-radical formation, observed during glutamate oxidation in an animal model of PD, needs to be further studied. Hence, elucidating the mechanisms by which estrogens regulate GDH activity may have important implications for understanding the role of these hormones in cell biology in health and disease and for the development of novel therapeutic approaches to human disorders.

While various embodiments of the invention have been described, it will be apparent to those of ordinary skill in the art that many more embodiments and implementations are possible that are within the scope of the invention.

I claim:

1. A method for diagnosis of susceptibility to early onset Parkinson's disease in humans comprising identifying a nucleic acid sequence exhibiting a polymorphism in the human GLUD2 gene, whereby that polymorphism consists of a substitution of guanine for thymine at position 309 of SEQ. ID. NO. 3.

2. A method according to claim 1 wherein the step of identifying such polymorphism consists of identifying the substitution of guanine for thymine at position 309 of SEQ. ID. NO. 3 and comparing the polymorphism to SEQ. ID. NO. 3.

3. A method according to claim 1, wherein the identifying step comprises the steps of obtaining a biological sample and testing that sample to identify a polymorphism in nucleic acid contained therein.

4. A method according to claim 3, wherein the identifying step comprises any of sequencing and probing the nucleic acid.

5. A method according to claim 4, wherein the identifying step comprises the step of amplifying a nucleic acid contained in the biological sample.

6. A method according to claim 1, wherein the identifying step comprises the steps of obtaining a biological sample and testing that sample to identify a variant protein therein associated with the polymorphism.

7. A method according to claim 6, comprising identifying a variant hGDH2 protein in which alanine is substituted for serine in the 104 position of SEQ ID NO. 4.

* * * * *

SEQUENCE LISTING

```
<160> NUMBER OF SEQ ID NOS: 4

<210> SEQ ID NO 1
<211> LENGTH: 2348
<212> TYPE: DNA
<213> ORGANISM: Homo sapiens

<400> SEQUENCE: 1
ttccttccta gtcgcgggga gtctgagaaa gcgcacctgt tccgcgaccg tcacgcaccc      60
ctcctccgcc tgccgcgatg taccgctacc tggccaaagc gctgctgccg tcccgggccg     120
ggcccgctgc cctgggctcc gcggccaacc actcggccgc gttgctgggc cggggccgcg     180
gacagcccgc cgccgcctcg cagccggggc tcgcattggc cgcccggcgc cactacagcg     240
agttggtggc cgaccgcgag gacgacccca acttcttcaa gatggtggag ggcttcttcg     300
atcgcggcgc cagcatcgtg gaggacaagt tggtgaagga cctgaggacc caggaaagcg     360
aggagcagaa gcggaaccgg gtgcgcggca tcctgcggat catcaagccc tgcaaccatg     420
tgctgagtct ctccttcccc atccggcgcg acgacggctc ctgggaggtc atcgaaggct     480
accgggccca gcacagccag caccgcacgc cctgcaaggg aggtatccgt tacagcactg     540
atgtgagtgt agatgaagta aaagctttgg cttctctgat gacatacaag tgtgcagtgg     600
```

```
ttgatgtgcc gtttgggggt gctaaagctg gtgttaagat caatcccaag aactataccg    660
aaaatgaatt ggaaaagatc acaaggaggt tcaccatgga gctagcaaag aagggcttta    720
ttggtcctgg cgttgatgtg cctgctccag acatgaacac aggtgagcgg agatgtcct     780
ggattgctga tacctatgcc agcaccatag ggcactatga tattaatgca cacgcctgtg    840
ttactggtaa acccatcagc caaggggaa tccatggacg catctctgct actggccgtg     900
gtgtcttcca tgggattgaa aacttcatca atgaagcttc ttacatgagc attttaggaa    960
tgacaccagg gtttagagat aaaacatttg ttgttcaggg atttggtaat gtgggcctac   1020
actctatgag atatttacat cgttttggtg ctaaatgtat tgctgttggt gagtctgatg   1080
ggagtatatg gaatccagat ggtattgacc caaaggaact ggaagacttc aaattgcaac   1140
atgggtccat tctgggcttc cccaaggcaa agccctatga aggaagcatc ttggaggtcg   1200
actgtgacat actgatccca gctgccactg agaagcagtt gaccaaatcc aacgcaccca   1260
gagtcaaagc caagatcatt gctgaaggtg ccaatgggcc aacaactcca gaagctgata   1320
agatcttcct ggagagaaac attttggtta ttccagatct ctacttgaat gctggaggag   1380
tgacagtatc ttactttgag tggctgaaga atctaaatca tgtcagctat ggccgtttga   1440
ccttcaaata tgaaagggat tctaactacc acttgctcct gtctgttcaa gagagtttag   1500
aaagaaaatt tggaaagcat ggtggaacta ttcccattgt acccacggca gagttccaag   1560
acagtatatc gggtgcatct gagaaagaca ttgtgcactc tgccttggca tacacaatgg   1620
agcgttctgc caggcaaatt atgcacacag ccatgaagta taacctggga ttggacctga   1680
gaacagctgc ctatgtcaat gccattgaaa aagtcttcaa agtgtacagt gaagctggtg   1740
tgaccttcac atagatggat catggctgac ttcctcacta acctcttcac gtgtaacttc   1800
tgcagaccta ccacaagttt acatgtaacc acagaaatcc ctttctctcc tgactcatta   1860
ctaatggata ccattctcaa caagtcaatc caaatcagcc cgttaaggag aaagaaatta   1920
atatacaagc tgagtgtgaa agtagaaatc acctacacca gagagctatt tggtattttt   1980
gcctttaaat aaaaagcctc ctccatatgg ctgtgcagcc ttgctctgtg cttttcccca   2040
gcacaatcag tgctagtgct ggggaaggga cagtcaagag cagtcagttg cttacttatt   2100
ttgctctgga tgagtctggg acacgctgta actttaacac atttaagaag aaggtgtgtg   2160
gccttttcag aaggtggcat ggtcctcaag tgagttctta gtatttata tcagcaaaat    2220
aactcaattt tgcagattgc aaacaaatat aaaagctgtt tctgtttatg aattttattc   2280
ttttagaata gaataagtac atgctgctgt aataaaattg cctttaatca cttaaaaaaa   2340
aaaaaaaa                                                            2348
```

<210> SEQ ID NO 2
<211> LENGTH: 558
<212> TYPE: PRT
<213> ORGANISM: Homo sapiens

<400> SEQUENCE: 2

Met Tyr Arg Tyr Leu Ala Lys Ala Leu Leu Pro Ser Arg Ala Gly Pro
1               5                   10                  15

Ala Ala Leu Gly Ser Ala Ala Asn His Ser Ala Ala Leu Leu Gly Arg
            20                  25                  30

Gly Arg Gly Gln Pro Ala Ala Ala Ser Gln Pro Gly Leu Ala Leu Ala
        35                  40                  45

Ala Arg Arg His Tyr Ser Glu Leu Val Ala Asp Arg Glu Asp Asp Pro
    50                  55                  60

```
Asn Phe Phe Lys Met Val Glu Gly Phe Asp Arg Gly Ala Ser Ile
 65                  70                  75                  80

Val Glu Asp Lys Leu Val Lys Asp Leu Arg Thr Gln Glu Ser Glu
                 85                  90                  95

Gln Lys Arg Asn Arg Val Arg Gly Ile Leu Arg Ile Ile Lys Pro Cys
            100                 105                 110

Asn His Val Leu Ser Leu Ser Phe Pro Ile Arg Arg Asp Asp Gly Ser
            115                 120                 125

Trp Glu Val Ile Glu Gly Tyr Arg Ala Gln His Ser Gln His Arg Thr
            130                 135                 140

Pro Cys Lys Gly Gly Ile Arg Tyr Ser Thr Asp Val Ser Val Asp Glu
145                 150                 155                 160

Val Lys Ala Leu Ala Ser Leu Met Thr Tyr Lys Cys Ala Val Val Asp
                165                 170                 175

Val Pro Phe Gly Gly Ala Lys Ala Gly Val Lys Ile Asn Pro Lys Asn
                180                 185                 190

Tyr Thr Glu Asn Glu Leu Glu Lys Ile Thr Arg Arg Phe Thr Met Glu
            195                 200                 205

Leu Ala Lys Lys Gly Phe Ile Gly Pro Gly Val Asp Val Pro Ala Pro
            210                 215                 220

Asp Met Asn Thr Gly Glu Arg Glu Met Ser Trp Ile Ala Asp Thr Tyr
225                 230                 235                 240

Ala Ser Thr Ile Gly His Tyr Asp Ile Asn Ala His Ala Cys Val Thr
                245                 250                 255

Gly Lys Pro Ile Ser Gln Gly Gly Ile His Gly Arg Ile Ser Ala Thr
                260                 265                 270

Gly Arg Gly Val Phe His Gly Ile Glu Asn Phe Ile Asn Glu Ala Ser
            275                 280                 285

Tyr Met Ser Ile Leu Gly Met Thr Pro Gly Phe Arg Asp Lys Thr Phe
            290                 295                 300

Val Val Gln Gly Phe Gly Asn Val Gly Leu His Ser Met Arg Tyr Leu
305                 310                 315                 320

His Arg Phe Gly Ala Lys Cys Ile Ala Val Gly Glu Ser Asp Gly Ser
                325                 330                 335

Ile Trp Asn Pro Asp Gly Ile Asp Pro Lys Glu Leu Glu Asp Phe Lys
            340                 345                 350

Leu Gln His Gly Ser Ile Leu Gly Phe Pro Lys Ala Lys Pro Tyr Glu
            355                 360                 365

Gly Ser Ile Leu Glu Val Asp Cys Asp Ile Leu Ile Pro Ala Ala Thr
            370                 375                 380

Glu Lys Gln Leu Thr Lys Ser Asn Ala Pro Arg Val Lys Ala Lys Ile
385                 390                 395                 400

Ile Ala Glu Gly Ala Asn Gly Pro Thr Thr Pro Glu Ala Asp Lys Ile
                405                 410                 415

Phe Leu Glu Arg Asn Ile Leu Val Ile Pro Asp Leu Tyr Leu Asn Ala
            420                 425                 430

Gly Gly Val Thr Val Ser Tyr Phe Glu Trp Leu Lys Asn Leu Asn His
            435                 440                 445

Val Ser Tyr Gly Arg Leu Thr Phe Lys Tyr Glu Arg Asp Ser Asn Tyr
            450                 455                 460

His Leu Leu Leu Ser Val Gln Glu Ser Leu Glu Arg Lys Phe Gly Lys
465                 470                 475                 480

His Gly Gly Thr Ile Pro Ile Val Pro Thr Ala Glu Phe Gln Asp Ser
```

```
                  485                 490                 495
Ile Ser Gly Ala Ser Glu Lys Asp Ile Val His Ser Ala Leu Ala Tyr
                500                 505                 510

Thr Met Glu Arg Ser Ala Arg Gln Ile Met His Thr Ala Met Lys Tyr
            515                 520                 525

Asn Leu Gly Leu Asp Leu Arg Thr Ala Ala Tyr Val Asn Ala Ile Glu
        530                 535                 540

Lys Val Phe Lys Val Tyr Ser Glu Ala Gly Val Thr Phe Thr
545                 550                 555

<210> SEQ ID NO 3
<211> LENGTH: 660
<212> TYPE: DNA
<213> ORGANISM: Homo sapiens

<400> SEQUENCE: 3
gagtcaaagc caagatcatt gctgaaggtg ccaatgggcc aacaactcca gaagctgata      60
agatcttcct ggagagaaac attttggtta ttccagatct ctacttgaat gctggaggag     120
tgacagtatc ttactttgag tggctgaaga atctaaatca tgtcagctat ggccgtttga     180
ccttcaaata tgaaagggat tctaactacc acttgctcct gtctgttcaa gagagtttag     240
aaagaaaatt tggaaagcat ggtggaacta ttcccattgt acccacggca gagttccaag     300
acagtatatc gggtgcatct gagaaagaca ttgtgcactc tgccttggca tacacaatgg     360
agcgttctgc caggcaaatt atgcacacag ccatgaagta taacctggga ttggacctga     420
gaacagctgc ctatgtcaat gccattgaaa aagtcttcaa agtgtacagt gaagctggtg     480
tgaccttcac atagatggat catggctgac ttcctcacta acctcttcac gtgtaacttc     540
tgcagaccta ccacaagttt acatgtaacc acagaaatcc ctttctctcc tgactcatta     600
ctaatggata ccattctcaa caagtcaatc caaatcagcc cgttaaggag aaagaaatta     660

<210> SEQ ID NO 4
<211> LENGTH: 164
<212> TYPE: PRT
<213> ORGANISM: Homo sapiens

<400> SEQUENCE: 4

Arg Val Lys Ala Lys Ile Ile Ala Glu Gly Ala Asn Gly Pro Thr Thr
1               5                   10                  15

Pro Glu Ala Asp Lys Ile Phe Leu Glu Arg Asn Ile Leu Val Ile Pro
            20                  25                  30

Asp Leu Tyr Leu Asn Ala Gly Gly Val Thr Val Ser Tyr Phe Glu Trp
        35                  40                  45

Leu Lys Asn Leu Asn His Val Ser Tyr Gly Arg Leu Thr Phe Lys Tyr
    50                  55                  60

Glu Arg Asp Ser Asn Tyr His Leu Leu Leu Ser Val Gln Glu Ser Leu
65                  70                  75                  80

Glu Arg Lys Phe Gly Lys His Gly Gly Thr Ile Pro Ile Val Pro Thr
                85                  90                  95

Ala Glu Phe Gln Asp Ser Ile Ser Gly Ala Ser Glu Lys Asp Ile Val
            100                 105                 110

His Ser Ala Leu Ala Tyr Thr Met Glu Arg Ser Ala Arg Gln Ile Met
        115                 120                 125
```

```
-continued

His Thr Ala Met Lys Tyr Asn Leu Gly Leu Asp Leu Arg Thr Ala Ala
    130                 135             140

Tyr Val Asn Ala Ile Glu Lys Val Phe Lys Val Tyr Ser Glu Ala Gly
145                 150             155                 160

Val Thr Phe Thr
```